(12) United States Patent
Alami et al.

(10) Patent No.: US 8,273,768 B2
(45) Date of Patent: Sep. 25, 2012

(54) ISO CA-4 AND ANALOGUES THEREOF AS POTENT CYTOTOXIC AGENTS INHIBITING TUBULINE POLYMERIZATION

(75) Inventors: Mouâd Alami, Bussy Saint Georges (FR); Jean-Daniel Brion, Saint Leu la Foret (FR); Olivier Provot, Sartrouville (FR); Jean-François Peyrat, Villebon sur Yvette (FR); Samir Messaoudi, Palaiseau (FR); Abdallah Hamze, Bourg la Reine (FR); Anne Giraud, Le Perreux sur Marne (FR); Jérôme Bignon, Le Val Saint Germain (FR); Joanna Bakala, Paris (FR); Jian-Miao Liu, Paris (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 363 days.

(21) Appl. No.: 12/594,495

(22) PCT Filed: Apr. 4, 2008

(86) PCT No.: PCT/EP2008/054118
§ 371 (c)(1),
(2), (4) Date: Oct. 2, 2009

(87) PCT Pub. No.: WO2008/122620
PCT Pub. Date: Oct. 16, 2008

(65) Prior Publication Data
US 2010/0129471 A1 May 27, 2010

(30) Foreign Application Priority Data
Apr. 4, 2007 (FR) .................................. 07 54280

(51) Int. Cl.
*A61K 31/47* (2006.01)
*C07D 215/14* (2006.01)
(52) U.S. Cl. ....................... 514/314; 546/165
(58) Field of Classification Search .................. 514/455, 514/314; 549/392; 546/165
See application file for complete search history.

(56) References Cited

U.S. PATENT DOCUMENTS

| 4,876,270 A | 10/1989 | Waespe |
| 5,430,062 A | 7/1995 | Cushman et al. |
| 5,466,861 A | 11/1995 | Dawson et al. |

FOREIGN PATENT DOCUMENTS

| EP | 0 278 915 A2 | 8/1988 |
| WO | WO 99/34788 A1 | 7/1999 |
| WO | WO 2004/078144 | 9/2004 |
| WO | WO 2006/026747 A2 | 3/2006 |

OTHER PUBLICATIONS

International Search Report issued for application No. PCT/EP2008/054118 on Jun. 12, 2008.
French Search Report issued for application No. FR 0754280 on Nov. 20, 2007.
Zhang et al., "The Synthetic Compound CC-5079 is a Potent Inhibitor of Tublulin Polymerization and Tumor Necrosis Factor-α Production with Antitumor Activity," *Cancer Res.*, vol. 66, No. 2, pp. 951-959, Jan. 15, 2006.
Gaskin et al., "Turbidimetric Studies of the in Vitro Assemble and Disassembly of Porcine Neurotubles,", *J. Mol. Biol.*, vol. 89, pp. 737-758, 1974.
Beauregard et al., "Differential sensitivity of two adenocarcinoma xenografts to the anti-vascular drugs combretastatin A4 phosphate and 5,6-dimethylxanthenone-4-acetic acid, assessed using MRI and MRS," *NMR Biomed.*, vol. 15, pp. 99-105, 2002.
Tron et al., "Medicinal Chemistry of Combretastatin A4: Present and Future Directions," *Journal of Medicinal Chemistry*, vol. 49, No. 11, pp. 3033-3044, Jun. 1, 2006.
Alvarez et al., "Isocombretastatins A: 1,1-Diarylethenes as potent inhibitors of tubulin polymerization and cytotoxic compounds," *Biooganic & Medicinal Chemistry*, vol. 17, pp. 6422-6431, 2009.
Database Caplus [Online] Chemical Abstracts Service, Columbus, Ohio, US, Bercot et al., "Synthesis of some .alpha.-alkyl derivatives of 3,4-dimethoxydiphenylmethane", XP002459022, 1962.
Database Caplus [Online] Chemical Abstracts Service, Columbus, Ohio, US, Bercot, "Synthesis of some .alpha.-alkyl derivatives of 3,4-dimethoxydiphenylmethane", XP002459023, 1963.
Database Caplus [Online] Chemical Abstracts Service, Columbus, Ohio, US, Ayguen et al., "Synthesis and biological evaluation of structural variants of carbazoquinocin C" XP002459024, 2003.
Database Beilstein [Online] Beilstein Institute for Organic Chemistry, Frankfurt-Main, DE, XP002459025, 1959.
Database Beilstein [Online] Beilstein Institute for Organic Chemistry, Frankfurt-Main, DE, XP002459026, 1899.
Database Beilstein [Online] Beilstein Institute for Organic Chemistry, Frankfurt-Main, DE, XP002459027, 1962.
Database Beilstein [Online] Beilstein Institute for Organic Chemistry, Frankfurt-Main, DE, XP002459028, 1963.
Database Caplus [Online] Chemical Abstracts Service, Columbus, Ohio, US, Gierer et al., "Comparative studies of the participation of different neighboring groups in the alkaline cleavage of .beta.-aryl ether bonds in lignins" XP002459030, 1983.
Database Beilstein [Online] Beilstein Institute for Organic Chemistry, Frankfurt-Main, DE, XP002459031, 2002.
Database Beilstein [Online] Beilstein Institute for Organic Chemistry, Frankfurt-Main, DE, XP002459032, 1925.
Database Caplus [Online] Chemical Abstracts Service, Columbus, Ohio, US, Nakova et al., "Synthesis of N-(arylethyl)arylthioacetamides according to the Willgerodt-Kindler reaction and their conversation into derivatives of 1-benzyl-1,2,3,4-tetrahydroisoquinoline" XP002459033, 1981.
Database Beilstein [Online] Beilstein Institute for Organic Chemistry, Frankfurt-Main, DE, XP002459034, 1975.

(Continued)

*Primary Examiner* — Taofiq A Solola
(74) *Attorney, Agent, or Firm* — Foley & Lardner LLP

(57) ABSTRACT

The invention relates to a compound of the formula (I) in which: $R_1$, $R_2$ and $R_3$ are independently a methoxy group optionally substituted by one or more fluorine atoms; $R_4$ is a hydrogen atom; $R_5$ and $R_6$ are identical and each represent a hydrogen or fluorine atom; A is a cycle selected from the group including aryl and heteroaryl groups, wherein said groups can be substituted.

20 Claims, 3 Drawing Sheets

OTHER PUBLICATIONS

Database Beilstein [Online] Beilstein Institute for Organic Chemistry, Frankfurt-Main, DE, XP002459035, 1947.

Petit et al., "Isolation and structure of combretastatin," *Canadian Journal of Chemistry*, vol. 60, pp. 1374-1376, 1982.

Shelanski et al., "Microtubule Assembly in the Absence of Added Nucleotides," *Proc. Nat. Acad. Sci.*, vol. 70, No. 3, pp. 765-768, Mar. 1973.

Iwasa et al., "Simple Isoquinoline and Benzylisoquinoline Alkaloids as Potential Antimicrobial, Antimalarial, Cytotoxic, and Anti-HIV Agents," *Bioorganic and Medicinal Chemistry*, vol. 9, pp. 2871-2884, 2001.

Al-Attar et al., "Synthese einiger auxochromhaltiger α, α-Diaryläthylene und Stilbene," *Helvetica Chimica Acta*, vol. 46, pp. 1286-1294, 1963.

Botella et al., "Synthesis of methylated resveratrol and analogues by Heck reactions in organic and aqueous solvents," *Tetrahedron*, vol. 60, pp. 5563-5570, 2004.

Popov et al., "Analysis of complexes of inhibitors with *Cryptosporidium hominis* DHFR leads to a new trimethoprim derivative," *Bioorganic & Medicinal Chemistry Letters*, vol. 16, pp. 4366-4370, 2006.

ISO CA-4 AND ANALOGUES THEREOF AS POTENT CYTOTOXIC AGENTS INHIBITING TUBULINE POLYMERIZATION

The invention relates to novel compounds, inhibitors of polymerization of tubulin useful for treating cancer, to their preparation methods as well as to their uses.

Cancer is the major cause of deaths worldwide after cardiovascular diseases. On a worldwide total of 58 million deaths registered in 2005, 7.6 million (i.e. 13%) were due to cancer. Very many efforts have been deployed these recent years as regards prevention, comfort brought to the patients and targeted treatments. Progress in medical oncology is mainly due to the understanding of different action mechanisms involved during cancers, but also to the development of many cytotoxic drugs either combined or not in polytherapy. For example mention may be made of cisplatin, anthracycline, methotrexate, 5FU, taxoids, irinotecan . . . ).

If surgery and radiotherapy are particularly effective treatments when cancer is limited to a single region of the body, chemotherapy becomes indispensable when the cancer cells are dispersed. Cytotoxic drugs may therefore be administered before a surgical operation or radiotherapy, in order to reduce the size of the tumor. They are very often used after these interventions in order to eliminate metastases and the whole of the cancer cells which would have resisted to these treatments.

If very many treatments based on cytotoxics have caused progress in medical research (combination of cytotoxics in order to avoid resistance phenomena, reduction of undesirable effects improving comfort of the patients), antitumoral chemotherapies need new efficient molecules for overcoming the phenomena of resistance to usual treatments which are increasingly and frequently encountered. Moreover, present drugs used in breast cancer (27.4% of the cases of cancers in women), lung cancer (13% of the cases and increasing in a breathtaking way in women), prostate cancer (15.5%), colon and rectum cancer (13%) allow a decrease in the seriousness level of tumors without however leading to total recoveries.

Among the main anticancer drugs used in human therapy, the agents interacting with tubulin occupy an important place. It is possible to distinguish two families of agents:

(a) taxans which act by inhibiting division of cancer cells thereby causing their death. They promote polymerization of tubulin, stabilization of non-functional microtubules and inhibit depolymerization thereof. These are paclitaxel (Taxol®) and docetaxel (Taxotere®). The latter is one of the chemotherapy agents the most used worldwide for treating breast cancer, lung cancer not with small cells and hormono-resistant metastatic prostate cancer; and (b) alkaloids from periwinkle, the binding of which to tubulin causes inhibition of polymerization into microtubules, thereby preventing the forming of the mitototic spindle. These are vincristine, vindesine, vinblastine and vinorelbine, which form on a worldwide basis nearly 10% of the market of cytotoxic antitumoral products.

Although they are effective, the use of taxans and Vinca alkaloids is limited by the development of resistance phenomena and induction of undesirable effects which therefore require routine monitoring. As an example, let us mention that vincristine has sensitomotor nerve toxicity while haematological toxicity is often the limiting factor in the case of treatment with vinblastine, vindesine or vinorelbine.

In front of the urgency of this situation, development of novel inhibitors has become a major challenge these recent years. The sought criteria for novel antitumoral compounds are:

1. the efficiency of the antitumoral activity on various strains in models in vitro but also in animal models in vivo,
2. the lifting of multi-resistance to drugs,
3. the design of water-soluble original molecules and if possible having a simple chemical structure,
4. the decrease in systemic toxicity,
5. the identification of the action mechanism.

In 1982, Pettit et al. (*Can. J. Chem.* 1982, 60, 1374-1376) isolated from the bark of *Combretum caffrum*, a South African willow from the family of Combretaceae, combrestatatin A-4 illustrated below.

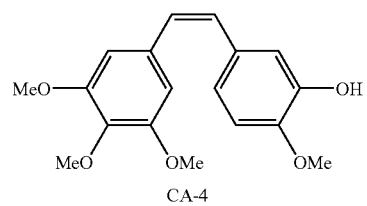

CA-4

This natural molecule of an extremely simple structure, is characterized by a stilbene unit of configuration Z substituted on the two aromatic rings with methoxy groups and a hydroxyl. The interest for this molecule raised by the scientific community is most particularly related to its antitumoral activities (cytotoxic and inhibiting effect on the polymerization of tubulin).

The first biological evaluations of combrestatatin A-4 (CA-4) have shown:

very potent cytotoxic activity on many cell lines with an $IC_{50}$ of the order of one nanomolar concentration (e.g.: $IC_{50}=0.9$ nM on HCT 15 cells). The cytotoxic activity of CA-4 was also studied on endothelial cells of human umbilical vein (HUVEC) and seems to involve a mechanism by apoptosis rather than by cell necrosis;

antimitotic activity (a spindle poison agent). It binds to tubulin on the binding site of Colchicine which has the consequence of inhibiting its polymerization into microtubules thereby preventing the formation of the mitotic spindle; and anti-angiogenic in vitro activity by inhibition of the proliferation of endothelial cells.

However, in vivo, the antitumoral activity of CA-4 decreases, or even totally disappears (for example, no antitumoral activity is observed on mouse colon adenocarcinoma 26). This lowering or absence of activity may be explained by the low solubility in water due to the lipophilicity of CA-4, which in vivo causes poor pharmacokinetics on the one hand, and by the ease of isomerization of the Z configuration double bond into E on the other hand. In this respect, it was shown that the E isomer of CA-4 has cytotoxic activity on mouse leukemic P-388 cells of about 60 times weaker than the natural Z isomer.

Because of the very simple chemical structure of CA-4 (as compared with those of Vinca alkaloids) and of its biological activities, many investigations have been conducted on this compound and today about 500 publications and more than 70 patent applications are listed.

Compounds analogous to CA-4 have been synthesized and evaluated. The molecules CA-4-P, OXI4503 and AVE-8062A illustrated below are presently developed in different laboratories.

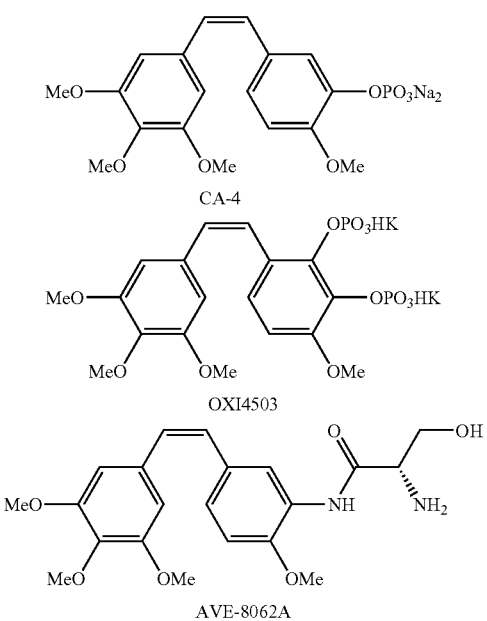

CA-4

OXI4503

AVE-8062A

However they have a double bond with a Z geometry which may lead to the biologically not very active E isomer.

International application WO 2006/026747 describes diphenylethylene derivatives fitting the following formula:

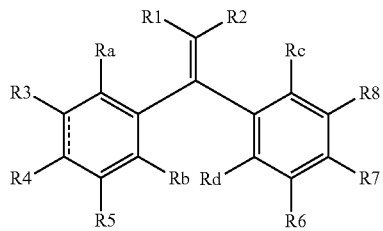

These compounds, which exist as E or Z isomers or as their mixtures, are described as being inhibitors of tubulin. Most of the cited examples are compounds for which the double bond is substituted, and in particular mono-substituted with a CN group (i.e. R1, R2=H, CN). However, no biological test has been conducted. It is therefore difficult to be able to evaluate the real anticancer potency of these compounds.

However, an article from the same team (Zhang et al. Cancer Res. 2006, 66(2), 951-959) describes the antitumoral activity of the compound CC-5079 having a CN substituent on the double bond, which would suggest that substitution of the double bond with this CN group is important for the therapeutic activity of these compounds.

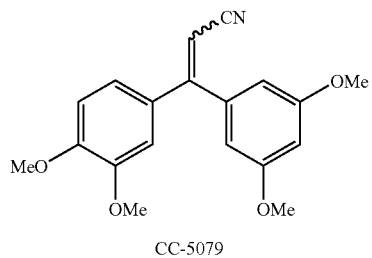

CC-5079

The applicant thus surprisingly discovered a novel family of compounds derived from CA-4 having strong cytotoxicity ($IC_{50}$ in the nanomolar range) on a large variety of human cancer cell lines, with inhibition of polymerization of tubulin at concentrations of the order of a micromolar concentration. Further, these novel compounds induce apoptosis, cause stopping of the cell cycle in the G2/M phase and have antivascular activities.

In a particularly interesting way, these compounds, called iso-CA-4, do not have any stereochemistry at the ethylenic double bond, and therefore cannot isomerize in vivo in order to lead to the less active E isomer.

More specifically, the object of the invention relates to compounds of the following formula (I):

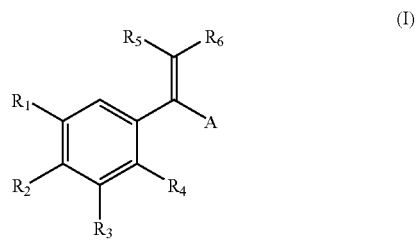

(I)

wherein:
$R_1$, $R_2$ and $R_3$ represent, independently of each other a methoxy group optionally substituted with one or more fluorine atoms,
$R_4$ represents a hydrogen atom,
$R_5$ and $R_6$ are identical and each represent a hydrogen or fluorine atom, and
A is a ring selected from the group comprising the aryl and heteroaryl groups, said groups may be:
either fused with a heterocycle including 5-7 members, optionally including one or more insaturations and optionally substituted with one or more $C_1$-$C_4$ alkyl groups,
or substituted with one or more groups selected from halogens, —B(OH)$_2$ groups, $C_1$-$C_4$ alkyls, $C_2$-$C_4$ alkenyls, $C_2$-$C_4$ alkynyls, aryl, heteroaryl, —COOH, —NO$_2$, methylenedioxy, —NR$_7$R$_8$, —NHCOR$_7$, —CONR$_7$R$_8$, —NHCOOR$_9$, —OSi(C$_1$-$C_4$ alkyl)$_3$, —NHSO$_2$R$_9$, $C_1$-$C_4$ alkoxy optionally substituted with one or more fluorine atoms, —OCONR$_7$R$_8$, —OSO$_2$CF$_3$, —OSO$_2$R$_9$, —SO$_2$R$_9$, —OSO$_3$H, —OPO(OR$_{10}$)$_2$, —ONR$_7$R$_8$, —OR$_{11}$, —SO$_2$NR$_{12}$R$_{13}$, —SO$_2$NHCOR$_{14}$, —OCOR$_{15}$, —OCOOR$_{16}$, —SR$_{17}$, —OCO(CH$_2$)$_n$C$_6$H$_4$N[(CH$_2$)$_m$Cl]$_2$ with n=1 to 4 and m=1 to 3, and a residue of a molecule with antitumoral activity bound via an ester or amide bond,
wherein:
$R_7$ and $R_8$ represent independently of each other, a hydrogen atom or a $C_1$-$C_4$ alkyl, aryl or heteroaryl group and advantageously represent a hydrogen atom or a $C_1$-$C_4$ alkyl group,
$R_9$ represents a $C_1$-$C_4$ alkyl, aryl or heteroaryl group and advantageously represents a $C_1$-$C_4$ alkyl group,
$R_{10}$ represents a hydrogen atom or a $C_1$-$C_4$ alkyl group or a benzyl group,
$R_{11}$ represents a hydrogen atom, an O-protective group, a sugar selected from glucose, mannose, arabinose or galactose, an aminosugar or an amino acid, the free OH and HN$_2$ groups of sugars, aminosugars and amino acids may optionally be substituted with an O-protective and N-protective group, respectively, $R_{12}$ and $R_{13}$ represent independently of each other a hydrogen atom, a $C_1$-$C_4$ alkyl group, an aryl or heteroaryl group, —$COR_{14}$ represents the remainder of an amino acid molecule bound to the —$SO_2NH$-group, or $R_{14}$ represents a $C_1$-$C_4$ alkyl group, $R_{15}$ represents a hydrogen atom, a $C_1$-$C_4$ alkyl, aryl or heteroaryl group, or a —$(CH_2)_m CO_2H$ or —$(CH_2)_m NR_7R_8$ group with m=1 to 3, $R_{16}$ represents a $C_1$-$C_4$ alkyl, aryl or heteroaryl group or a —$(CH_2)_m CO_2H$ or —$(CH_2)_m NR_7R_8$ group with m=1 to 3, and $R_{17}$ represents a hydrogen atom or a $C_1$-$C_4$ alkyl or aryl group, as well as its pharmaceutically acceptable salts and its prodrugs, excluding the compounds of the following formulae:

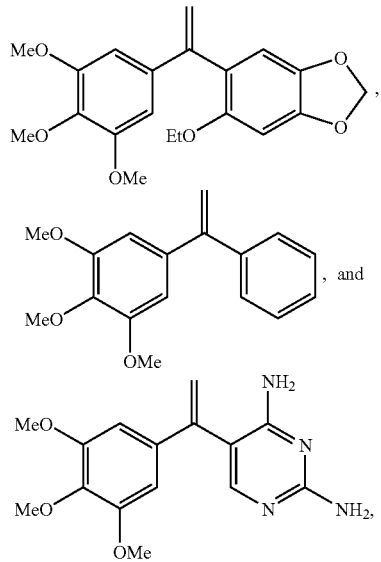

By the term of "halogen", is meant in the sense of the present invention, the fluorine, chlorine, bromine and iodine atoms.

By the term of "$C_1$-$C_4$ alkyl group" is meant in the sense of the present invention any linear or branched hydrocarbon group including 1-4 carbon atoms, in particular the methyl, ethyl, n-propyl, isopropyl, n-butyl, iso-butyl, sec-butyl and tert-butyl groups.

By the term of "$C_2$-$C_4$ alkenyl group" is meant in the sense of the present invention any linear or branched hydrocarbon group including 2-4 carbon atoms, and including at least one double bond, such as a vinyl (ethynyl) group.

By the term of "$C_2$-$C_4$ alkynyl group", is meant in the sense of the present invention any linear or branched hydrocarbon group including 2-4 carbon atoms and including at least one triple bond, such as an ethynyl or propynyl group.

By the term of "$C_1$-$C_4$ alkoxy group", is meant in the sense of the present invention any linear or branched O-alkyl group including 1-4 carbon atoms, in particular the methoxy, ethoxy, propoxy, n-butoxy, iso-butoxy and tert-butoxy groups.

By the term of "aryl group", is meant in the sense of the present invention one or more aromatic rings having from 5 to 10 carbon atoms, which may be fused. In particular, the aryl groups may be monocyclic or bicyclic groups such as for example the phenyl or naphthyl group. Advantageously the aryl group is a phenyl.

By the term of "heteroaryl group", is meant in the sense of the present invention, any aromatic group comprising from 5 to 10 ring atoms, which are carbon atoms or one or more heteroatoms, such as for example sulfur, nitrogen or oxygen atoms. The heteroaryl according to the present invention may be formed with one or two fused rings. Examples of heteroaryl groups are the quinolyl, isoquinolyl, imidazolyl, indolyl, pyridyl, triazinyl, thiazoyl, pyridazinyl, and thiophenyl groups.

By the term of "heterocycle", is meant in the sense of the present invention any hydrocarbon ring, either saturated or not, but not aromatic, of 5 to 7 members containing one or more heteroatoms, such as for example sulfur, nitrogen or oxygen atoms.

Within the scope of the present invention, the group formed by a heterocycle fused with an aryl group, may advantageously be a chromanyl, a chromenyl or a 1,3-benzo-dioxolyl.

By "sugar", is notably meant in the sense of the present invention, erythrose, threose, ribose, arabinose, xylose, lyxose, allose, altrose, glucose, mannose, gulose, idose, galactose, talose, erythrulose, ribulose, xylulose, psicose, fructose, sorbose, or further tagatose, in the D or L form. Advantageously, this is glucose, mannose, arabinose or galactose.

By "aminosugar", is meant in the sense of the present invention a sugar in which an amino group replaces a hydroxyl group, such as for example glucosamine and galactosamine.

By "amino acid", in the sense of the present invention, are meant all the residues of natural α-amino acids (for example Alanine (Ala), Arginine (Arg), Asparagine (Asn), Aspartic acid (Asp), Cysteine (Cys), Glutamine (Gln), Glutamic acid (Glu), Glycine (Gly), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr) and Valine (Val)) in the D or L form, as well as non-natural amino acids (for example (1-naphthyl)-alanine, (2-naphthyl)alanine, homophenylalanine, (4-chloro-phenyl)-alanine, (4-fluorophenyl)alanine, (3-pyridyl)-alanine, phenylglycine, diaminopimelic acid, 2,6-diamino-heptane-1,7-dioic acid, 2-aminobutyric acid, 2-aminotetralin-2-carboxylic acid, erythro-β-methylphenylalanine, threo-β-methylphenyl-alanine, (2-methoxyphenyl) alanine, 1-amino-5-hydroxyindane-2-carboxylic acid, 2-aminoheptane-1,7-dioic acid, (2,6-dimethyl-4-hydroxyphenyl)alanine, erythro-β-methyltyrosine or threo-β-methyltyrosine).

By the term of "O-protective group", is meant in the sense of the present invention any substituent which protects the hydroxyl or carboxyl group, i.e. a reactive oxygen atom, against undesirable reactions, such as the O-protective groups described in Greene, "Protective Groups In Organic Synthesis", (John Wiley & Sons, New York (1981)) and Harrison et al. "Compendium of Synthetic Organic Methods", Vols. 1 to 8 (J. Wiley & Sons, 1971 to 1996). The O-protective groups comprise methyl or alkyl ethers, either substituted or not, for example, methoxymethyl, benzyloxymethyl, 2-methoxyethoxy-methyl, 2-(trimethylsilyl)-ethoxymethyl, t-butyl, benzyl and triphenylmethyl, benzyl ethers (either substituted or not), tetrahydropyranyl ethers, allyl ethers, substituted ethyl ethers, for example, 2,2,2-trichloroethyl, silyl ethers or alkylsilyl ethers, for example, trimethylsilyl, t-butyl-dimethylsilyl and t-butyl-diphenylsilyl, heterocycle ethers and esters prepared by reaction of the hydroxyl group with a carboxylic acid for example, tert-butyl, benzyl or methyl esters, carbonates, in particular benzyl or haloalkyl carbonate, acetate, propionate, benzoate and the like. Advantageously, this is a tert-butyl, an acetyl or a benzyl.

By the term of "N-protective group", is meant in the sense of the present invention any substituent which protects the $NH_2$ group against undesirable reactions, such as the N-protective groups described in Greene, "Protective Groups In Organic Synthesis", (John Wiley & Sons, New York (1981)) and Harrison et al. "Compendium of Synthetic Organic Methods", Vols. 1 to 8 (J. Wiley & Sons, 1971 to 1996). The N-protective groups comprise carbamates, amides, N-alkylated derivatives, amino acetal derivatives, N-benzylated derivatives, imine derivatives, enamine derivatives and N-heteroatom derivatives. In particular, the N-protective group comprises formyl, acetyl, benzoyl, pivaloyl, phenylsulfonyl, benzyl (Bn), t-butyloxycarbonyl (Boc), benzyloxycarbonyl (Cbz), 9-fluorenylmethoxycarbonyl (Fmoc), p-methoxybenzyloxycarbonyl, p-nitrobenzyl-oxycarbonyl, trichloroethoxycarbonyl (TROC), allyloxycarbonyl (Alloc), 9-fluorenylmethyloxycarbonyl (Fmoc), trifluoro-acetyl, benzyl carbamates (either substituted or not) and the like. Advantageously, this is the Fmoc group.

By "ester or amide bond", is meant a —C(O)O— or —C(O)NH— group. In the particular case of the present invention, the carbonyl of the ester or amide bond will preferentially be bound to the residue of the molecule having antitumoral activity while the oxygen or the NH group of this same bond will be bound to the aryl or heteroaryl group defined in A.

In the present invention, by "pharmaceutically acceptable" it is intended to designate what is useful in the preparation of a pharmaceutical composition, which is generally safe, non-toxic and neither biologically nor otherwise undesirable and which is acceptable for veterinary use as well as for human pharmaceutically use.

The term of "pharmaceutically acceptable salts" of a compound is meant to designate salts which are pharmaceutically acceptable, as defined herein, and which have the desired pharmacological activity of the parent compound. Such salts comprise:

(1) hydrates and solvates, (2) acid addition salts formed with inorganic acids such as hydrochloric acid, hydrobromic acid, sulfuric acid, nitric acid, phosphoric acid and the like; or formed with organic acids such as acetic acid, benzene sulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid, and the like. Advantageously, this is hydrochloric acid; or (3) the salts formed when an acid proton present in the parent compound is either replaced with a metal ion, for example an alkaline metal ion, an earth alkaline metal ion; or is coordinated with an organic or inorganic base. The acceptable organic bases comprise diethanolamine, ethanolamine, N-methylglucamine, triethanolamine, tromethamine and the like. The acceptable inorganic bases comprise aluminium hydroxide, calcium hydroxide, potassium hydroxide, sodium carbonate and sodium hydroxide. Advantageously, the acid proton is displaced by a $Na^+$ ion, notably while using sodium hydroxide.

The acid addition salts are in particular formed with an amine function or with a pyridine. Base addition salts are in particular formed with a carboxylic acid function (—COOH), phosphate function (—OP(O)(OH)$_2$) or further sulfate function (—OSO$_3$H).

The term of "prodrug" is meant to designate in the sense of the present invention a compound which is administered in an inactive (or less active) form and which is metabolized in vivo, notably by action of enzymes or of gastric acid, into an active (or more active) form. The use of a prodrug allows in particular improvement in the physico-chemical parameters of a molecule such as solubility as well as pharmacokinetics (vectorization, bioavailability, etc.), in order to promote its assimilation by an organism after administration. In particular, a prodrug of a molecule bearing an amino group ($NH_2$) may notably result from acylation or phosphorylation of this amino group. When a molecule bears a hydroxy group (OH), the prodrug may in particular result from acylation or phosphorylation of this hydroxy group.

Advantageously $R_1$, $R_2$ and $R_3$ each represent a methoxy group.

Also advantageously, $R_5$ and $R_6$ each represent a hydrogen atom.

Advantageously, $R_1$, $R_2$ and $R_3$ each represent a methoxy group and $R_5$ and $R_6$ each represent a hydrogen atom.

Also advantageously $R_5$ and $R_6$ each represent a fluorine atom.

Advantageously, $R_1$, $R_2$ and $R_3$ each represent a methoxy group and $R_5$ and $R_6$ each represent a fluorine atom.

Still more advantageously, the molecule with antitumoral activity will be a molecule with anti-vascular, cytotoxic, anti-angiogenic, anti-apoptotic or kinase inhibitory activity. In particular, it may be selected from 6-mercaptopurine, fludarabine, cladribine, pentostatin, cytarabine, 5-fluorouracil, gemcitabine, methotrexate, raltitrexed, irinotecan, topotecan, etoposide, daunorubicin, doxorubicin, epirubicin, idarubicin, pirarubicin, mitoxantrone, chlormethine, cyclophosphamide, ifosfamide, melphalan, chlorambucil, busulfan, carmustine, fotemustine, streptozocine, carboplatine, cisplatine, oxaliplatine, procarbazine, dacarbazine, bleomycin, vinblastine, vincristine, vindesine, vinorelbine, paclitaxel, docetaxel, L-asparaginase, flutamide, nilutamide, bicalutamide, cyproterone acetate, triptorelin, leuprorelin, goserelin, buserelin, formestane, aminoglutethimide, anastrazole, letrozole, tamoxifene, octreotide, lanreotide, (Z)-3-[2,4-dimethyl-5-(2-oxo-1,2-dihydro-indol-3-ylidènemethyl)-1H-pyrrol-3-yl]-propionic acid (SU 6668), 4-((9-chloro-7-(2,6-difluorophenyl)-5H-pyrimidol(5,4-d)(2)benzazepin-2-yl)amino) benzoic acid (MLN-8054), 5,6-dimethylxanthenone-4-acetic acid (DMXAA) or further 3-(4-(1,2-diphenylbut-1-enyl)phenyl)acrylic acid (GW 5638). Advantageously, this is DMXAA.

Advantageously the molecule with antitumoral activity will include a carboxylic acid function COOH, such as SU 6668, MLN-8054, DMXAA or GW 5638, thereby allowing it to be coupled to the aryl or heteroaryl group of A, substituted with at least one OH or $NH_2$ group, through an esterification or amidification reaction. A molecule with antitumoral activity may however be used, on which an acid function will be grafted in order to allow coupling with the aryl or heteroaryl group of A.

The thereby formed ester or amide bond has the advantage of being easily hydrolysable in vivo. Thus, after administration of the compound of the invention, the molecule with antitumoral activity as well as a novel molecule of the invention, may be released, allowing dual therapeutic action.

In a particular embodiment, A is selected from the group comprising phenyl, naphthyl, quinolinyl and indolyl, and preferably phenyl, said groups may be:

either fused with a heterocycle including 5 to 7 members, optionally including one or more insaturations and optionally substituted with one or more $C_1$-$C_4$ alkyl groups, or substituted with one or more groups selected from halogens, —B(OH)$_2$ groups, $C_1$-$C_4$ alkyls, $C_2$-$C_4$ alkenyls, $C_2$-$C_4$ alkynyls, aryl, heteroaryl, —COOH, —NO$_2$, methylenedioxy, —NR$_7$R$_8$, —NHCOR$_7$, —CONR$_7$R$_8$, —NHCOOR$_9$, —OSi($C_1$-$C_4$ alkyl)$_3$, —NHSO$_2$R$_9$, $C_1$-$C_4$ alkoxy optionally substituted with one or more fluorine atoms, —OCONR$_7$R$_8$, —OSO$_2$CF$_3$, —OSO$_2$R$_9$, —SO$_2$R$_9$, —OSO$_3$H, —OPO(OR$_{10}$)$_2$, —ONR$_7$R$_8$, —OR$_{11}$, —SO$_2$NR$_{12}$R$_{13}$, —SO$_2$NHCOR$_{14}$, —OCOR$_{15}$, —OCOOR$_{16}$, —SR$_{17}$, —OCO(CH$_2$)$_n$C$_6$H$_4$N[(CH$_2$)$_m$Cl]$_2$ with n=1 to 4 and m=1 to 3, and a residue of a molecule with antitumoral activity bound via an ester or amide bond, R$_7$, R$_8$, R$_9$, R$_{10}$, R$_{11}$, R$_{12}$, R$_{13}$, R$_{14}$, R$_{15}$, R$_{16}$, and R$_{17}$ being as defined above.

Advantageously, A is a ring selected from the group comprising aryl and heteroaryl groups, said ring may be substituted with one or more groups selected from -Me, —OH, —OMe, —OCF$_3$, —NH$_2$, —NO$_2$, —COOH, —B (OH)$_2$, —OSitBuMe$_2$, —OCOMe, —OCOtBu, methylenedioxy, —OCONEt$_2$, —OCO(CH$_2$)$_2$COOH, —OCOCH$_2$NMe$_2$, —OSO$_3$H, —OSO$_2$CF$_3$, —OP(O)(OH)$_2$, —OP(O)(OEt)$_2$, —OPO(OCH$_2$Ph)$_2$, —Br, —F, —OCO(CH$_2$)$_3$C$_6$H$_4$N[(CH$_2$)$_2$Cl]$_2$, —OCO(C$_5$H$_4$N),

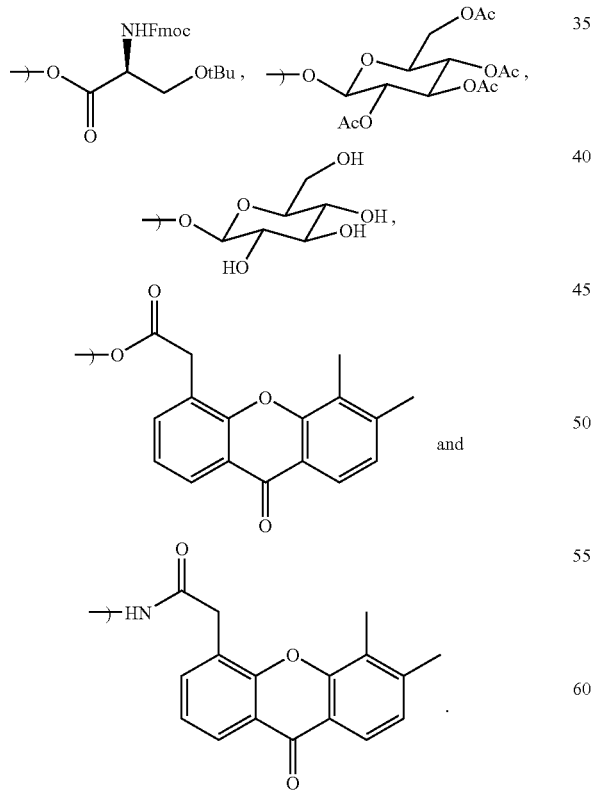

A represents in a still more advantageous way, a phenyl, naphthyl, quinolinyl or indolyl, and preferably phenyl group, said group may be substituted with one or more groups selected from -Me, —OH, —OMe, —OCF$_3$, —NH$_2$, —NO$_2$, —COOH, —B (OH)$_2$, —OSitBuMe$_2$, —OCOMe, —OCOtBu, methylenedioxy, —OCONEt$_2$, —OCO(CH$_2$)$_2$COOH, —OCOCH$_2$NMe$_2$, —OSO$_3$H, —OSO$_2$CF$_3$, —OP(O)(OH)$_2$, —OP(O)(OEt)$_2$, —OPO(OCH$_2$Ph)$_2$, —Br, —F, —OCO(CH$_2$)$_3$C$_6$H$_4$N[(CH$_2$)$_2$Cl]$_2$, —OCO(C$_5$H$_4$N),

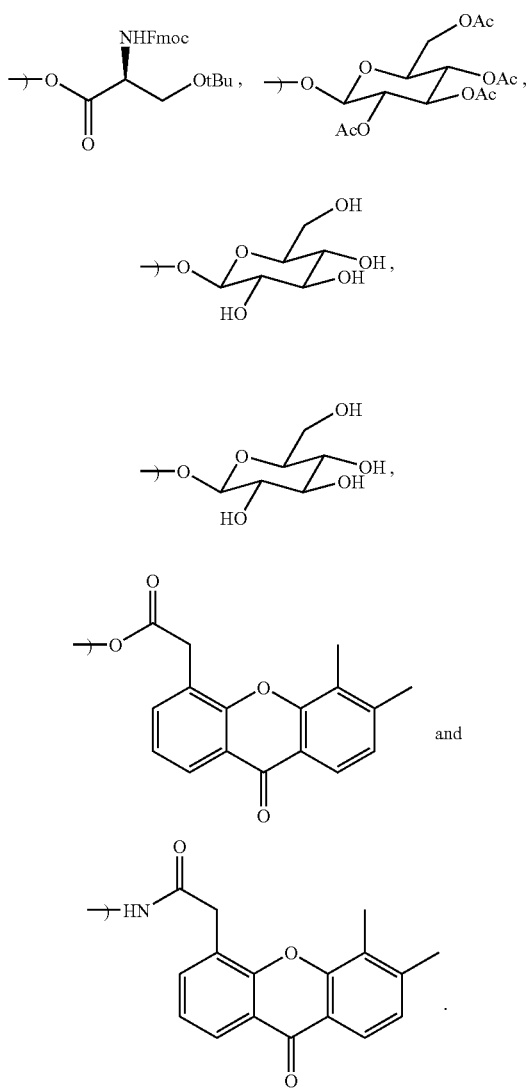

A also advantageously represents an aryl or heteroaryl group, advantageously a phenyl or naphthyl group, preferably a phenyl group, said groups may be substituted with one or more groups selected from the group comprising ethyl, propyl, butyl, —NH$_2$, —NHMe, —NMe$_2$, —NMeEt, —NHEt, —NEt$_2$, —NHCOMe, —NHCOEt, —CONH$_2$, —CONMe$_2$, —CONEt$_2$, —OSiMe$_3$, —OSiEt$_3$, —NHCO$_2$Me, —NHCO$_2$Et, —OCH$_2$F, —OCHF$_2$, —OEt, —OCOEt, —SO$_2$Me, —SO$_2$Et, —OP(O)(OMe)$_2$, —OP(O)(OEt)$_2$, —ONH$_2$, —ONMe$_2$, —ONEt$_2$, —SO$_2$NH$_2$, —SO$_2$NMe$_2$, —SO$_2$NEt$_2$, —SO$_2$NMeEt, —SO$_2$NHMe, —SO$_2$NHEt, —SO$_2$NHCOMe, —SO$_2$NHCOEt.

Advantageously, the compounds of the invention fit the following formula II:

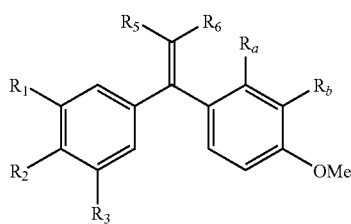

(II)

wherein:

$R_1$, $R_2$, $R_3$, $R_5$ and $R_6$ are as defined above, $R_a$ represents a hydrogen or halogen atom, or a group —B(OH)$_2$, $C_1$-$C_4$ alkyls, $C_2$-$C_4$ alkenyls, $C_2$-$C_4$ alkynyls, aryl, heteroaryl, —COOH, —NO$_2$, methylenedioxy, —NR$_7$R$_8$, —NHCOR$_7$, —CONR$_7$R$_8$, —NHCOOR$_9$, —OSi(C$_1$-C$_4$ alkyl)$_3$, —NHSO$_2$R$_9$, $C_1$-$C_4$ alkoxy optionally substituted with one or more fluorine atoms, —OCONR$_7$R$_8$, —OSO$_2$CF$_3$, —OSO$_2$R$_9$, —SO$_2$R$_9$, —OSO$_3$H, —OPO(OR$_{10}$)$_2$, —ONR$_7$R$_8$, —OR$_{11}$, —SO$_2$NR$_{12}$R$_{13}$, —SO$_2$NHCOR$_{14}$, —OCOR$_{15}$, —OCOOR$_{16}$, —SR$_{17}$, or —OCO(CH$_2$)$_n$C$_6$H$_4$N[(CH$_2$)$_m$Cl]$_2$ with n=1 to 4 and m=1 to 3, and $R_b$ represents a halogen atom, and preferably a fluorine atom, a —OR$_{11}$, —OCOR$_{15}$, —OCOOR$_{15}$, —OCONR$_7$R$_8$, —OSO$_2$R$_9$, —OSO$_2$CF$_3$, —OSO$_3$H, —OPO(OR$_{10}$)$_2$, —NH$_2$, —NHCOR$_7$, —NHCOOR$_9$, —NHSO$_2$R$_9$ group, or a residue of a molecule with antitumoral activity bound via an ester or amide bond, $R_7$, $R_8$, $R_9$, $R_{10}$, $R_{11}$, $R_{12}$, $R_{13}$, $R_{14}$, $R_{15}$, $R_{16}$ and $R_{17}$ being as defined above.

Advantageously, $R_a$ represents a hydrogen atom or a —NR$_7$R$_8$, —NHCOR$_7$, —CONR$_7$R$_8$, —NHCOOR$_9$, —NHSO$_2$R$_9$, —OCONR$_7$R$_8$, —OSO$_2$CF$_3$, —OSO$_2$R$_9$, —OSO$_3$H, —OPO(OR$_{10}$)$_2$, —ONR$_7$R$_8$, —OR$_{11}$, —SO$_2$NR$_{12}$R$_{13}$, —SO$_2$NHCOR$_{14}$, —OCOR$_{15}$ or —OCOOR$_{16}$ group, with $R_7$, $R_8$, $R_9$, $R_{10}$, $R_{11}$, $R_{12}$, $R_{13}$, $R_{14}$, $R_{15}$, and $R_{16}$ as defined above.

Still more advantageously, $R_a$ represents a hydrogen atom or a —NR$_7$R$_8$, —NHCOR$_7$, —OCONR$_7$R$_8$, —NHCOOR$_9$, —OCONR$_7$R$_8$, —OPO(OR$_{10}$)$_2$, —OCOR$_{15}$ or —OCOOR$_{16}$ group, with $R_7$, $R_8$, $R_9$, $R_{10}$, $R_{15}$, and $R_{16}$ as defined above.

Still more advantageously, $R_a$ represents a hydrogen atom.

In particular, the compounds of the invention may be selected from:

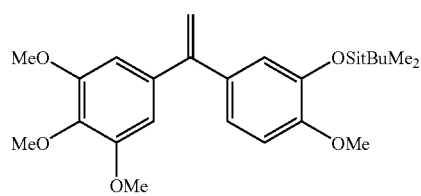

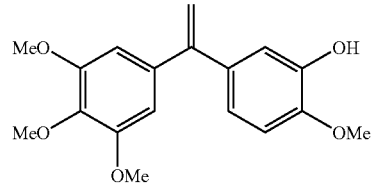

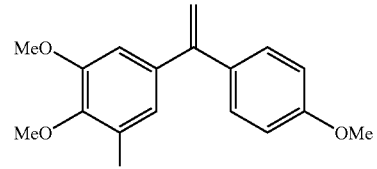

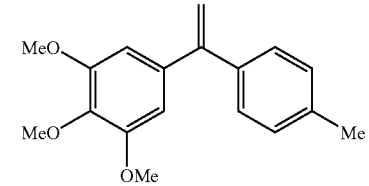

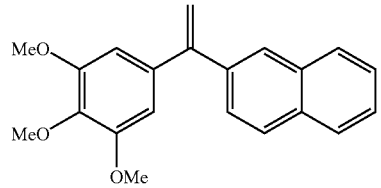

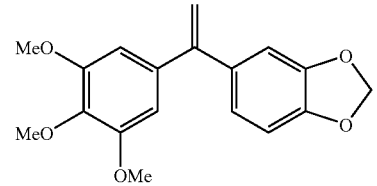

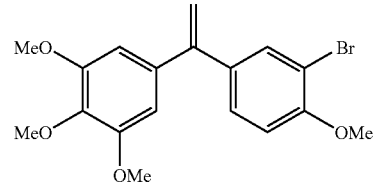

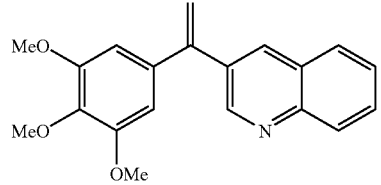

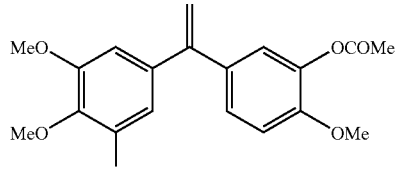

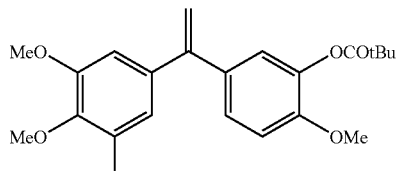

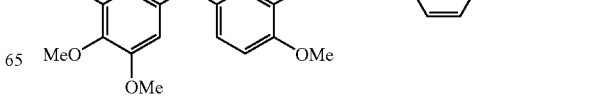

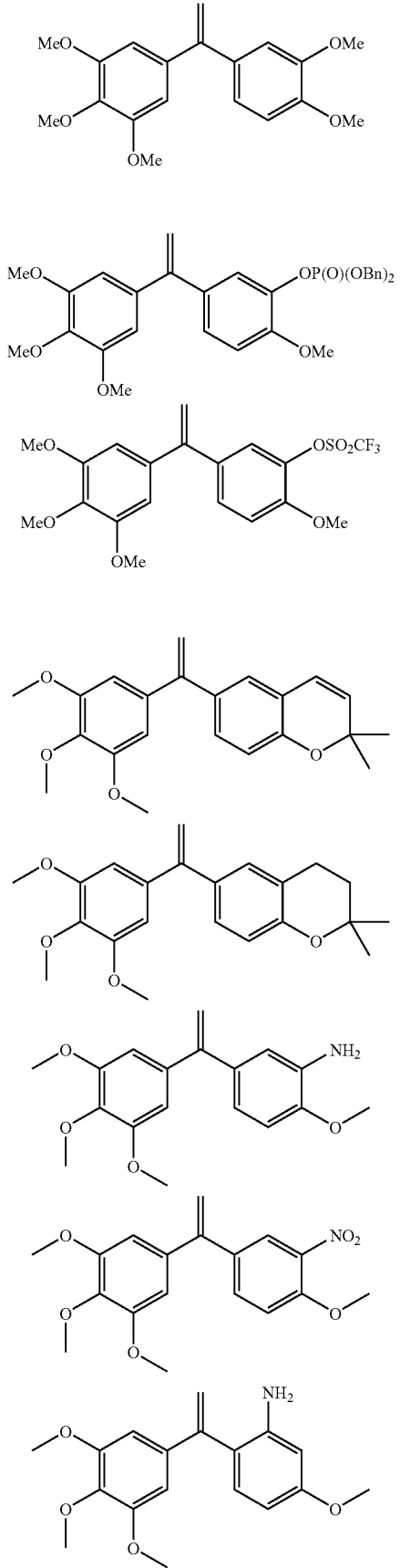
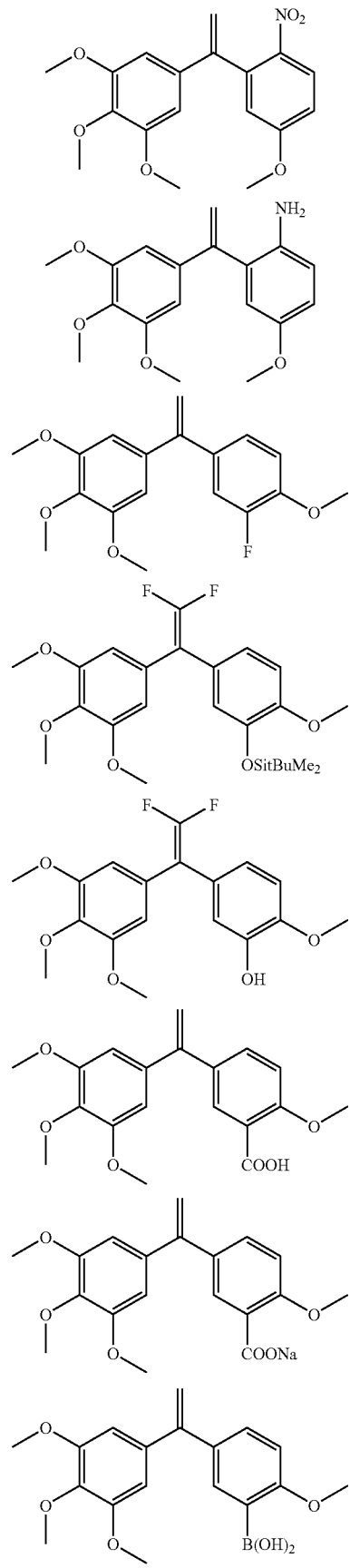

-continued
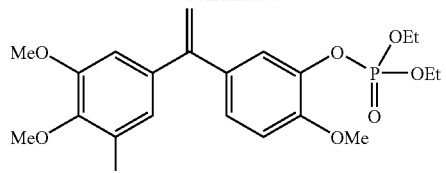
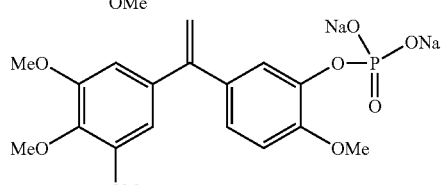
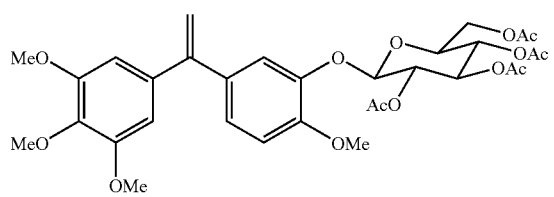
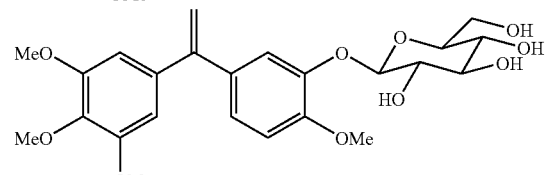
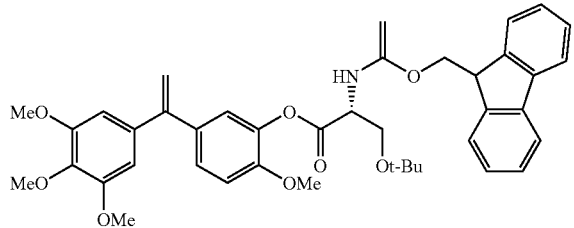
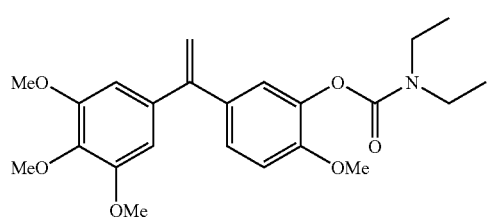
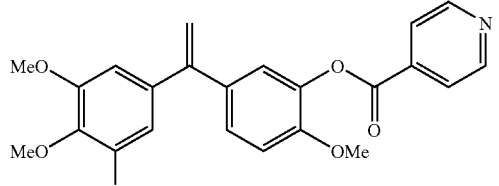
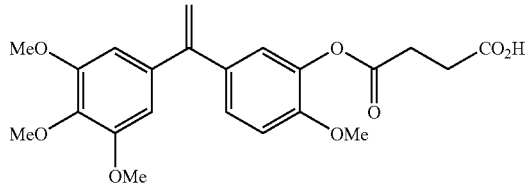
-continued
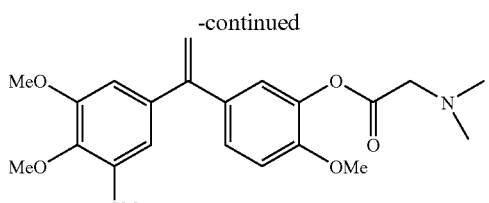
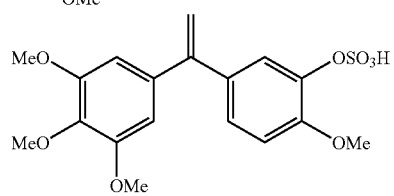
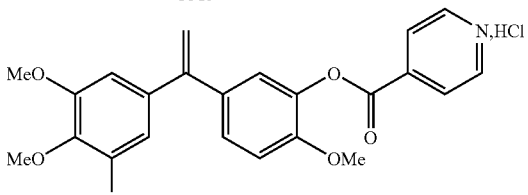
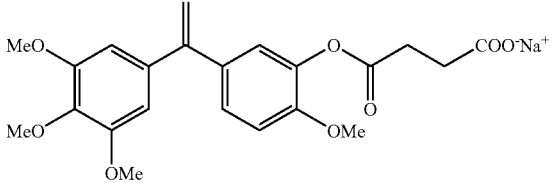
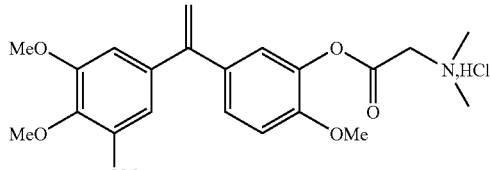
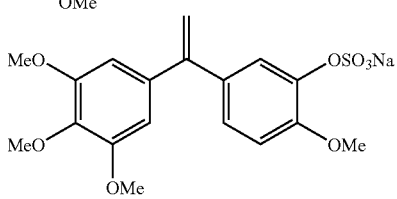
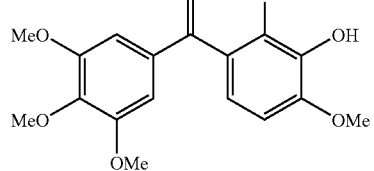
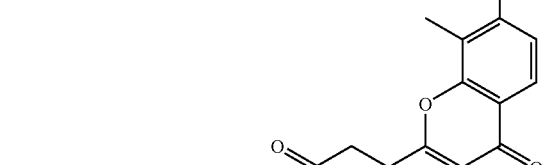
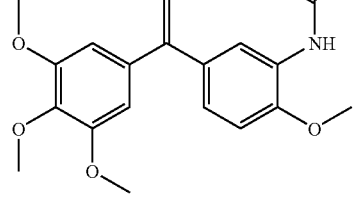

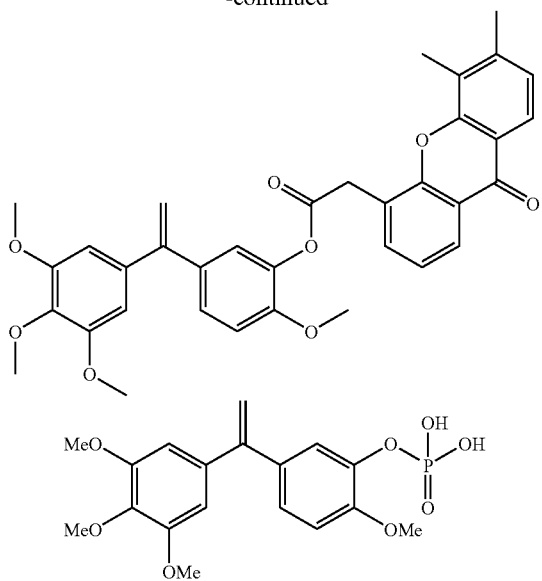

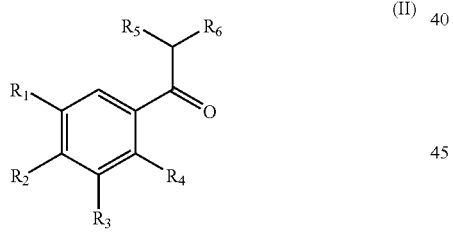

The absence of stereochemistry of the double bond of the compounds of formula (I), definitively solves the problem of isomerization which may be involved in vitro, causing drops (or absence) of cytotoxic activity as this is the case of CA-4 for example.

The object of the invention also relates to the methods for the synthesis of compounds of formula (I).

The compounds of formula (I) may be synthesized according to methods known to one skilled in the art, from products commercially available or prepared according to methods known to one skilled in the art, and in particular according to any method comprising the following successive steps:

reacting a compound of the following formula (II):

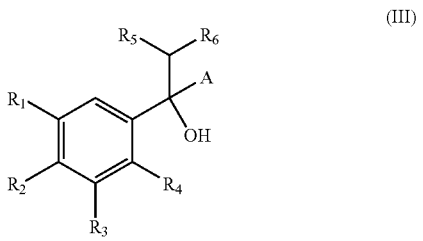

wherein $R_1$, $R_2$, $R_1$, $R_3$, $R_4$, $R_5$ and $R_6$ are as defined earlier, with an organometallic compound of formula A-M wherein A is as defined earlier and M represents an alkaline metal or an earth alkaline metal substituted with a halogen, in order to form the compound of the following formula (III):

(III)

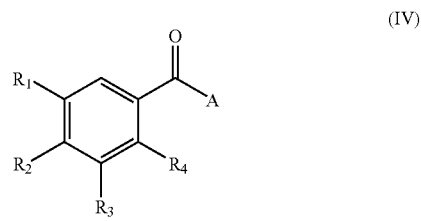

reacting the thereby obtained compound of formula (III) with an acid in order to form the corresponding compound of formula (I);

followed by optional additional conventional steps for modifying the substituents of A.

By "alkaline metal", is notably meant sodium (Na), lithium (Li) or potassium (K).

By "earth alkaline metal" is notably meant calcium (Ca) or magnesium (Mg).

Advantageously, M represents the lithium atom or the group MgX where X represents a halogen, preferably bromine or chlorine, and advantageously bromine.

Also advantageously, the acid used in the last step is para-toluenesulfonic acid (APTS).

The compounds of formula (I) may also be prepared from the compound of the following formula (IV):

(IV)

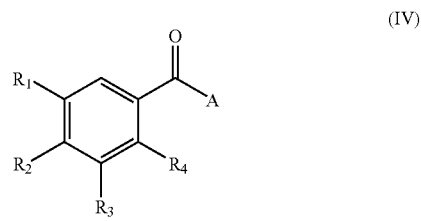

for which $R_1$, $R_2$, $R_3$, $R_4$ and A are as defined earlier, by a Wittig reaction, in the presence of methyl triphenylphosphonium bromide or chloride (in the case when $R_5$=$R_6$=H) or ethyl difluoromethyl phosphonate (in the case when $R_5$=$R_6$=F), and in the presence of a base, this reaction may optionally be followed by additional conventional steps for modifying the substituents of A.

Advantageously, the base used for the Wittig reaction will be lithium hexamethyldisilazide (LiHMDS).

The compound of formula (IV) may notably be obtained by oxidation of the corresponding alcohol of the following formula (V):

(V)

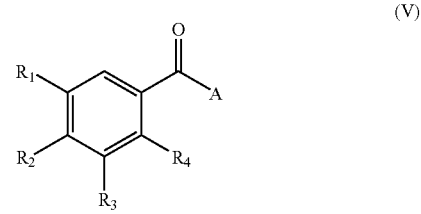

for which $R_1$, $R_2$, $R_3$, $R_4$ and A are as defined earlier, by using for example manganese oxide or pyridinium chlorochromate (PCC).

The alcohol (V) may itself be obtained from the aldehyde of the following formula (VI):

(VI)

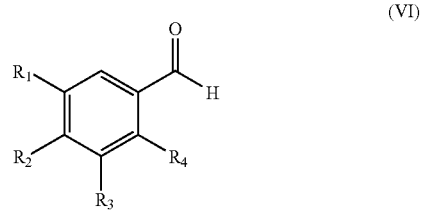

for which $R_1$, $R_2$, $R_3$, and $R_4$ are as defined earlier, by reaction with an organometallic compound of formula A-M wherein A and M are as defined earlier.

The synthesis steps are thus compatible with industrial requirements. Moreover, the thereby prepared analogs (sugar, phosphates, boronic acids, . . . ) are soluble in water and may be assimilated orally.

The object of the invention is also compounds of formulae (I) or compounds selected from

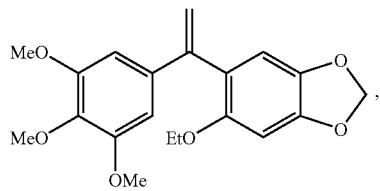

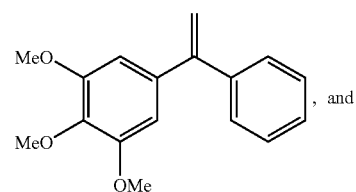

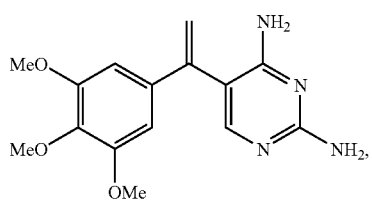

as well as their pharmaceutically acceptable salts and their prodrugs, as drugs, advantageously as drugs inhibiting polymerization of tubulin, and still advantageously as drugs intended for treating or preventing proliferative diseases such as cancer, psoriasis or fibrosis, and in particular cancer.

In particular, the compounds of the invention may be used for the treatment of a cancer, such as those capable of being treated by CA-4 or by taxotere.

The invention also relates to the use of a compound of formula (I) or a compound selected from:

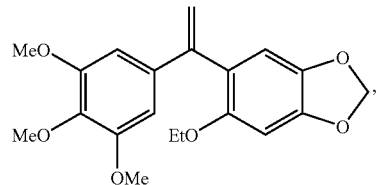

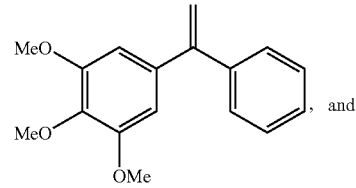

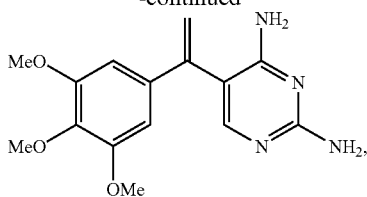

or one of their pharmaceutically acceptable salts or their prodrugs, for making a drug inhibiting polymerization of tubulin, and advantageously intended for treating or preventing proliferative diseases such as cancer, psoriasis or fibrosis, and in particular cancer.

The object of the invention is also a pharmaceutical composition comprising at least one compound of formula (I) or one compound selected from

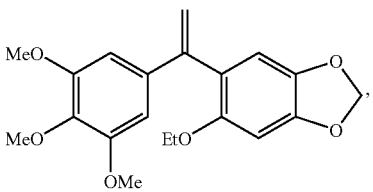

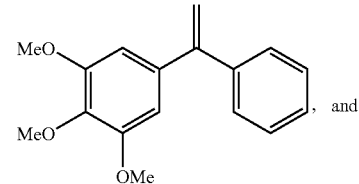

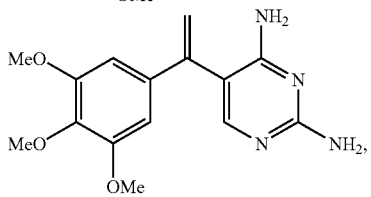

or one of their pharmaceutically acceptable salts or their prodrugs, in association with one or more pharmaceutically acceptable excipients.

The object of the invention is also a pharmaceutical composition comprising at least one compound of formula (I) or one compound selected from

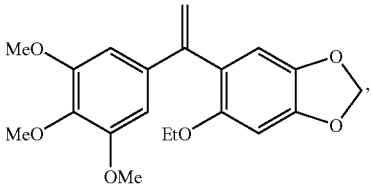

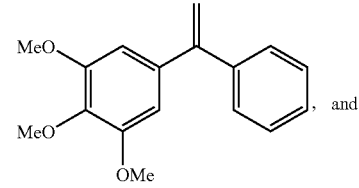

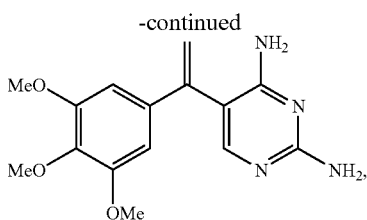

or one of their pharmaceutically acceptable salts or their prodrugs, in association with at least one other active ingredient, notably an anticancer, either cytotoxic or not, compound, in association with one or more pharmaceutically acceptable excipients.

As examples of active ingredients which may be associated with the compound of formula (I), in a non-limiting way, mention is made of 6-mercaptopurine, fludarabine, cladribine, pentostatin, cytarabine, 5-fluorouracil, gemcitabine, methotrexate, raltitrexed, irinotecan, topotecan, etoposide, daunorubicin, doxorubicin, epirubicin, idarubicin, pirarubicin, mitoxantrone, chlormethine, cyclophosphamide, ifosfamide, melphalan, chlorambucil, busulfan, carmustine, fotemustine, streptozocine, carboplatine, cisplatine, oxaliplatine, procarbazine, dacarbazine, bleomycin, vinblastine, vincristine, vindesine, vinorelbine, paclitaxel, docetaxel, L-asparaginase, flutamide, nilutamide, bicalutamide, cyproterone acetate, triptorelin, leuprorelin, goserelin, buserelin, formestane, aminoglutethimide, anastrazole, letrozole, tamoxifene, octreotide, lanreotide, (Z)-3-[2,4-dimethyl-5-(2-oxo-1,2-dihydro-indol-3-ylidènemethyl)-1H-pyrrol-3-yl]-propionic acid, 4-((9-chloro-7-(2,6-difluorophenyl)-5H-pyrimidol(5,4-d)(2)benzazepin-2-yl)amino)benzoic acid, 5,6-dimethylxanthenone-4-acetic acid or further 3-(4-(1,2-diphenylbut-1-enyl)phenyl)acrylic acid.

The compounds according to the invention may be administered via an oral, sublingual, parenteral, subcutaneous, intramuscular, intravenous, transdermal, local or rectal route.

The compounds according to the invention may be used in the treatment and prevention of proliferative diseases such as cancers, psoriasis and fibrosis.

They may be used in doses comprised between 0.01 mg and 1,000 mg daily, given as a single dose once a day, or preferably administered in several doses all along the day, for example twice a day in equal doses. The daily administered dose is advantageously comprised between 5 mg and 500 mg, still more advantageously between 10 mg and 200 mg. The use of doses outside these ranges may be necessary, which one skilled in the art may himself/herself realize.

The compounds according to the invention may be used for decreasing or inhibiting polymerization of tubulin, notably in vivo or in vitro.

The object of the present invention is also a pharmaceutical composition comprising:
(i) at least one compound of formula (I) or a compound selected from

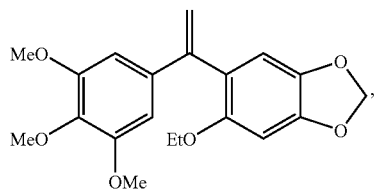

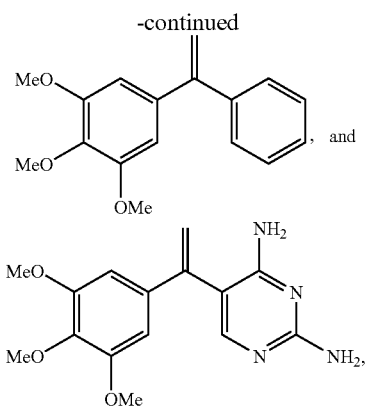

(ii) at least one other active ingredient, notably useful for treating proliferative diseases such as cancer, psoriasis or fibrosis, and advantageously an anticancer agent such as an antivascular, cytotoxic or anti-angiogenic agent,
as combination products for simultaneous, separate use, or use spread out in time.

As an active ingredient, mention may notably be made in a non-limiting way of 6-mercaptopurine, fludarabine, cladribine, pentostatin, cytarabine, 5-fluorouracil, gemcitabine, methotrexate, raltitrexed, irinotecan, topotecan, etoposide, daunorubicin, doxorubicin, epirubicin, idarubicin, pirarubicin, mitoxantrone, chlormethine, cyclophosphamide, ifosfamide, melphalan, chlorambucil, busulfan, carmustine, fotemustine, streptozocine, carboplatine, cisplatine, oxaliplatine, procarbazine, dacarbazine, bleomycin, vinblastine, vincristine, vindesine, vinorelbine, paclitaxel, docetaxel, L-asparaginase, flutamide, nilutamide, bicalutamide, cyproterone acetate, triptorelin, leuprorelin, goserelin, buserelin, formestane, aminoglutethimide, anastrazole, letrozole, tamoxifene, octreotide, lanreotide, (Z)-3-[2,4-dimethyl-5-(2-oxo-1,2-dihydro-indol-3-ylidènemethyl)-1H-pyrrol-3-yl]-propionic acid, 4-((9-chloro-7-(2,6-difluorophenyl)-5H-pyrimidol(5,4-d)(2)benzazepin-2-yl)amino)benzoic acid, 5,6-dimethylxanthenone-4-acetic acid or further 3-(4-(1,2-diphenylbut-1-enyl)phenyl)acrylic acid.

The pharmaceutical composition as described, may be in particular useful for treating proliferative diseases, such as cancer, psoriasis or fibrosis, and in particular cancer.

The present invention also relates to the use of a pharmaceutical composition comprising:
(iii) at least one compound of formula (I) or a compound selected from

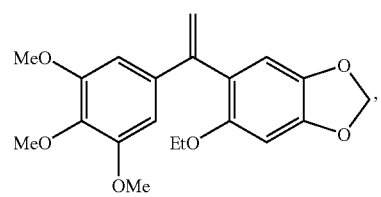

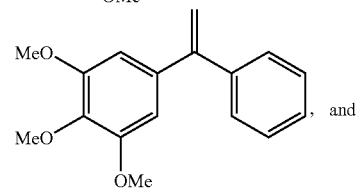

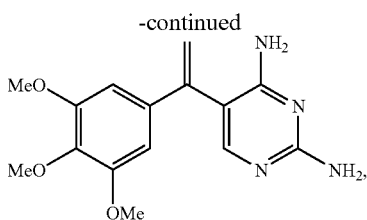

(iv) at least one other active ingredient, notably useful for the treatment of proliferative diseases such as cancer, psoriasis or fibrosis, and advantageously an anticancer agent such as an antivascular, cytotoxic or anti-angiogenic agent,
as combination products for simultaneous, separate use or use spread out over time, for making a drug intended for the treatment of proliferative diseases, such as cancer, psoriasis or fibrosis, and in particular cancer.

The invention will now be illustrated in a non-limiting way, by Examples 1 to 5 and FIGS. 1 to 5 which follow.

FIG. 1 illustrates the effect of the compound (I-1) on the distribution of the investigated cells according to different phases of the cell cycle after 24 hours of treatment.

FIG. 2 illustrates induction of apoptosis in leukemic cells (K562, HTC116, MDA-MB 231) treated for hours with the compound (I-I). Apoptosis is demonstrated by measuring the enzymatic activity of caspases 3 and 7 and the results are expressed in % relatively to the cells treated for 24 hours with 0.1% DMSO.

EXAMPLE 1

Synthesis 1.1. Compound of Formula (I-5)

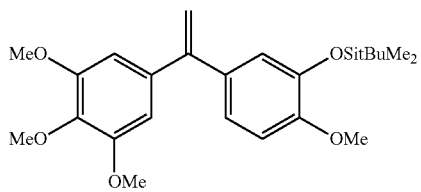

Figure 1:
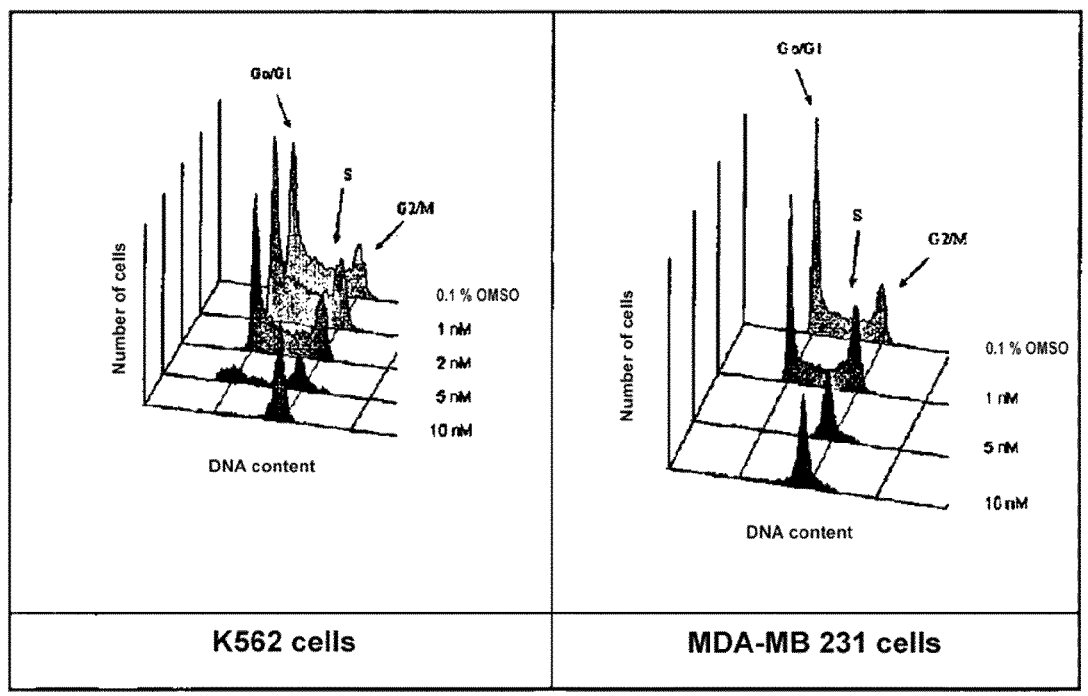

At −78° C., 1 mmol of tBuLi (2 eq.) is added to a solution containing 0.5 mmol of tbutyl[(5-iodo-2-methoxybenzyl)]-dimethylsilane dissolved in 15 mL of distilled hexane. After 45 minutes of stirring at this temperature, 0.5 mmol of 3,4,5-trimethoxyacetophenone diluted in 5 mL of distilled toluene is added. This mixture is stirred for 12 hours while allowing the temperature to gradually rise and then is slowly hydrolyzed by a saturated $NH_4Cl$ solution up to a pH=7-8. After extraction with diethylether (3×20 mL), the collected organic phases are dried on $Na_2SO_4$ and concentrated in the rotary evaporator. The raw reaction product is taken up in 10 mL of $CH_2Cl_2$ to which are added a few grains of hydrated para-toluenesulfonic acid, (APTS) and then is stirred for 3 hours at room temperature. The solution is washed with NaCl saturated solution, extracted with $CH_2Cl_2$. After drying on $Na_2SO_4$ and concentration in the rotary evaporator, an oil is collected which is purified on silica gel. Yield 55%.

$H^1$ NMR: δ ppm, $CD_3COCD_3$ 300 MHz: 0.15 (s, 6H), 0.98 (s, 9H), 3.75 (s, 3H), 3.78 (s, 3H), 3.95 (s, 3H), 5.33 (d, 1H, J=1.2 Hz), 5.34 (d, 1H, J=1.2 Hz), 6.60 (s, 2H), 6.83 (t, 1H, J=1.2 Hz), 6.96 (m, 2H). Elemental analysis: (MM=430.22) Calculated C, 66.94; H, 7.96. Found C, 66.85; H, 7.92.

1.2. Compound of Formula (I-1)

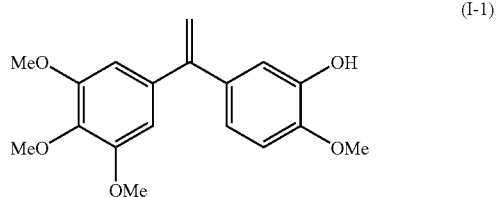

The silylated compound (I-5) (0.17 mmol) is dissolved in 10 mL of methanol to which is added 0.25 mmol of $K_2CO_3$. The solution is stirred at room temperature for 12 hours and then washed with a saturated NaCl solution. The aqueous phase is extracted with ethyl acetate (3×10 mL). The collected organic phases are dried on $Na_2SO_4$ and concentrated in the rotary evaporator in order to obtain a residue purified on silica gel. Yield 94%.

$H^1$ NMR: δ ppm, $CDCl_3$, 300 MHz: 3.81 (s, 6H), 3.87 (s, 3H), 3.91 (s, 3H), 5.30 (d, 1H, J=1.5 Hz), 5.37 (d, 1H, J=1.5 Hz), 5.60 (bs, 1H), 6.55 (s, 2H), 6.82 (m, 2H), 6.97 (d, 1H, J=2.1 Hz). Mass spectroscopy (ESI) $[M+Na]^+$=339. Elemental analysis: (MM=316.13) Calculated C, 68.34; H, 6.37. Found C, 68.25; H, 6.33.

1.3. Synthesis of Compounds (I-2), (I-3) and (I-4) by Action of Commercial Grignard Reagents 1.3.1. Compound of Formula (I-2)

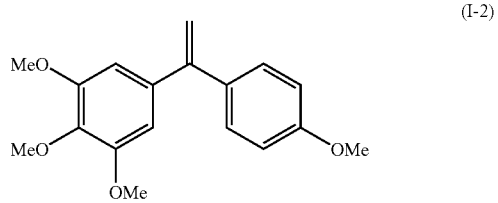

At 0° C. and under an argon atmosphere, a commercial solution of (4-methoxyphenyl)magnesium bromide (2.2 mmol) is slowly added dropwise to a solution containing 1 mmol of 3,4,5-trimethoxy-acetophenone diluted in 5 mL of distilled tetrahydrofurane (THF). The solution is stirred for 12 hours at room temperature and then hydrolyzed by adding a saturated $NH_4Cl$ solution up to a pH=7-8. After extraction with dichloromethane (3×20 mL), the collected organic phases are dried on $Na_2SO_4$ and concentrated in the rotary evaporator. The raw reaction product is then treated like for (I-1) with para-toluenesulfonic acid in order to lead after purification on silica gel to the expected derivative. Yield 64%.

H$^1$ NMR: δ ppm, CD$_3$COCD$_3$, 300 MHz: 3.75 (s, 3H), 3.78 (s, 6H), 3.82 (s, 3H), 5.34 (m, 2H), 6.60 (s, 2H), 6.92 (d, 2H, J=8.7 Hz), 7.29 (d, 2H, J=8.7 Hz). Elemental analysis: (MM=300.14) Calculated C, 71.98; H, 6.71. Found C, 71.85; H, 6.66.

1.3.2. Compound of Formula (I-3)

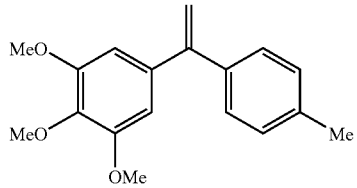

(I-3)

It was prepared according to the operating procedure described for the compound of formula (I-2) from ortho-tolylmagnesium bromide and from 3,4,5-trimethoxyacetophenone. Yield 54%.

H$^1$ NMR: δ ppm, CD$_3$COCD$_3$, 300 MHz: 2.33 (s, 3H), 3.75 (s, 3H), 3.76 (s, 6H), 5.38 (d, 1H, J=1.2 Hz), 5.40 (d, 1H, J=1.2 Hz), 6.59 (s, 2H), 7.22-7.25 (m, 4H). Elemental analysis: (MM=284.14) Calculated C, 76.03; H, 7.09. Found C, 75.74; H, 6.99.

1.3.3. Compound of Formula (I-4)

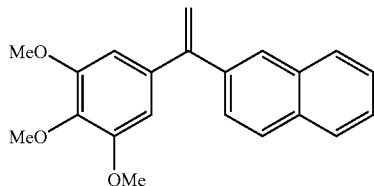

(I-4)

It was prepared from 2-naphthylmagnesium bromide and from 3,4,5-trimethoxyacetophenone according to the operating procedure described for the compound of formula (I-2). Yield 81%.

H$^1$ NMR: δ ppm, CD$_3$COCD$_3$ 300 MHz: 3.77 (s, 9H), 5.54-5.64 (m, 2H), 6.67 (s, 2H), 7.50-7.55 (m, 3H), 7.87-7.91 (m, 4H). Elemental analysis: (MM=320.14) Calculated C, 78.73; H, 6.29. Found C, 78.64; H, 6.20.

1.4. Compound of Formula (I-10)

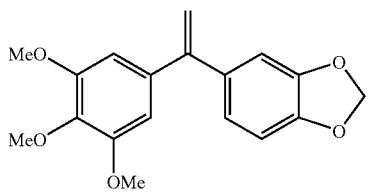

(I-10)

At −78° C., 1 mmol of tBuLi (2 eq.) is added to a solution containing 0.5 mmol of 5-bromo-benzo[1,3]dioxole dissolved in 15 mL of distilled hexane. After 45 minutes of stirring at this temperature, 0.5 mmol of 3,4,5-trimethoxyacetophenone diluted in 5 ml of distilled toluene is added. This mixture is stirred for 12 hours while letting the temperature rise up gradually and is then slowly hydrolyzed with a saturated NH$_4$Cl solution up to a pH=7-8. After extraction with diethylether (3×20 mL), the collected organic phases are dried on Na$_2$SO$_4$ and concentrated in the rotary evaporator. The raw reactional product is taken up in 10 mL of CH$_2$Cl$_2$ to which are added a few grams of hydrated APTS and is then stirred for 3 hours at room temperature. The solution is washed with a saturated NaCl solution, extracted with CH$_2$Cl$_2$. After drying on Na$_2$SO$_4$ and concentration in the rotary evaporator, an oil is collected which is purified on silica gel. Yield 19%.

H$^1$ NMR: δ ppm, CDCl$_3$ 300 MHz: 3.72 (s, 6H), 3.78 (s, 3H), 5.21 (d, 1H, J=1.5 Hz), 5.25 (d, 1H, J=1.5 Hz), 5.86 (s, 2H), 6.46 (s, 2H), 6.67 (d, 1H, J=8.7 Hz), 6.72-6.76 (m, 2H). Mass spectroscopy (ESI) [M+Na]$^+$=337. Elemental analysis: (MM=314.12) Calculated C, 68.78; H, 5.77. Found C, 68.68; H, 5.72.

1.5. Compound of Formula (I-13)

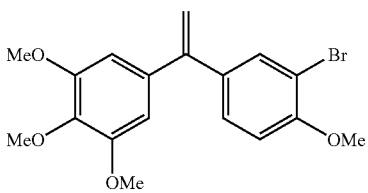

(I-13)

At −100° C., 1 mmol of nBuLi (1 eq.) is added to a solution containing 1 mmol of 2-bromo-4-iodo-1-methoxy-benzene dissolved in 15 mL of distilled hexane. After 45 minutes of stirring at this temperature, 0.5 mmol of 3,4,5-trimethoxyacetophenone diluted in 5 ml of distilled toluene is added. This mixture is stirred for hours while letting the temperature rise up gradually and is then slowly hydrolyzed by a saturated NH$_4$Cl solution up to a pH=7-8. After extraction with diethylether (3×20 mL), the collected organic phases are dried on Na$_2$SO$_4$ and concentrated in the rotary evaporator. The raw reaction product is taken up in 10 mL of CH$_2$Cl$_2$ to which a few grains of hydrated APTS is added, and then stirred for 3 hours at room temperature. The solution is washed with a saturated NaCl solution, extracted with CH$_2$Cl$_{24}$. After drying on Na$_2$SO$_4$ and concentration in the rotary evaporator, an oil is collected which is purified on silica gel. Yield 53%.

H$^1$ NMR: δ ppm, CDCl$_3$ 300 MHz: 3.65 (s, 3H), 3.78 (s, 6H), 3.85 (s, 3H), 5.30 (s, 1H), 5.70 (s, 1H), 6.50 (s, 2H), 6.80 (d, 1H, J=8.7 Hz), 7.36-7.46 (m, 2H). Mass spectroscopy (ESI) [M+Na]$^+$=403. Elemental analysis: (MM=378.05) Calculated C, 57.01; H, 5.05. Found C, 56.78; H, 4.90.

1.6. Compound of Formula (I-14)

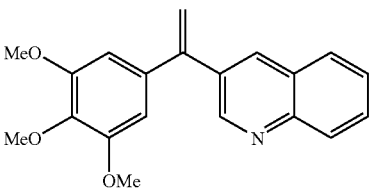

(I-14)

At −100° C., 1 mmol of nBuLi (1 eq.) is added to a solution containing 1 mmol of 3-bromoquinoline dissolved in 15 mL of distilled diethylether. After 2 hours of stirring at this temperature, 1 mmol of 3,4,5-trimethoxyacetophenone diluted in 5 mL of diethylether is added. This mixture is stirred for 2 hours while letting the temperature rise up gradually and is then slowly hydrolyzed by a saturated NH₄Cl solution up to a pH=7-8. After extraction with diethylether (3×20 mL), the collected organic phases are dried on Na₂SO₄ and concentrated in the rotary evaporator. The raw reaction product is taken up in 10 mL of CH₂Cl₂ to which 4 mmol of dimethylaminopyridine (DMAP) and 2.4 mmol of mesyl chloride are added. The whole is stirred for 1 hour at room temperature and the solution is washed with a saturated NaCl solution and then extracted with CH₂Cl₂. After concentration, the raw reaction product is again taken up in 15 mL of CH₂Cl₂ to which 27 mmol of 1,8-diazabicyclo[5.4.0]undec-7-ene (DBU) are added. The whole is refluxed for 3 hours. After washing with an NaCl solution, extraction with CH₂Cl₂ and drying on Na₂SO₄, a white solid is collected which is purified on silica gel. Overall yield 36%.

H¹ NMR: δ ppm, CDCl₂, 300 MHz: 3.77 (s, 6H), 3.80 (s, 3H), 5.52 (s, 2H), 6.51 (s, 2H), 7.41-7.50 (t, 1H, J=6.9 Hz), 7.60-7.64 (t, 1H, J=6.9 Hz), 7.72 (d, 1H, J=6.9 Hz), 7.96-8.08 (m, 2H), 8.88 (d, 1H, J=2.1 Hz). Elemental analysis: (MM=321.14) Calculated C, 74.75; H, 5.96. Found C, 74.61; H, 5.90.

1.7. Compound of Formula (I-6)

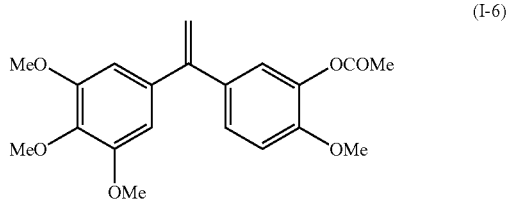

(I-6)

To a solution of the compound (I-1) (0.316 mmol) dissolved in 1 mL of CH₂Cl₂ are added 54 μL of pyridine and 0.016 mmol of DMAP. The mixture is cooled to 0° C. and 42 μL of acetic anhydride (0.442 mmol) are slowly added. After 1 hour of stirring at 0° C., the reaction mixture is hydrolyzed (H₂O, 3 mL) and then extracted with ethyl acetate (3×3 mL). The organic phases are collected, dried on sodium sulfate and concentrated in order to obtain a residue which is purified on silica gel. Yield 65%.

H¹ NMR: δ ppm, CDCl₂, 300 MHz: 2.28 (s, 3H), 3.74 (s, 6H), 3.78 (s, 3H), 3.84 (s, 3H), 5.26 (d, 1H, J=1.5 Hz), 5.31 (d, 1H, J=1.5 Hz), 6.48 (s, 2H), 6.86 (d, 1H, J=8.7 Hz), 6.97 (d, 1H, J=2.1 Hz), 7.16 (dd, 1H, J=8.4 Hz, J=2.1 Hz). Mass spectroscopy (ESI) [M+Na]⁺=381. Elemental analysis: (MM=358.14) Calculated C, 67.03; H, 6.19. Found C, 66.88; H, 6.06.

1.8. Compound of Formula (I-7)

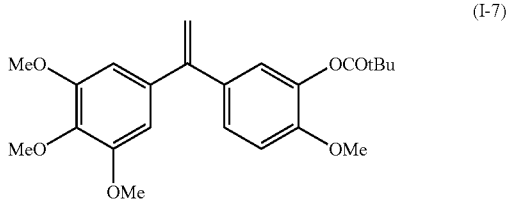

(I-7)

The compound (I-7) was prepared similarly to (I-6) from pivaloic anhydride. Yield 74%.

H¹ NMR: δ ppm, CDCl₃, 300 MHz: 1.28 (s, 9H), 3.74 (s, 6H), 3.80 (s, 3H), 3.84 (s, 3H), 5.26 (d, 1H, J=1.5 Hz), 5.30 (d, 1H, J=1.5 Hz), 6.48 (s, 2H), 6.82 (d, 1H, J=12.6 Hz), 6.95 (d, 1H, J=3.3 Hz), 7.10 (dd, 1H, J=12.6 Hz, J=3.3 Hz). Mass spectroscopy (ESI) [M+Na]⁺=423. Elemental analysis: (MM=400.19) Calculated C, 68.98; H, 7.05. Found C, 68.69; H, 6.96.

1.9. Compound of Formula (I-8)

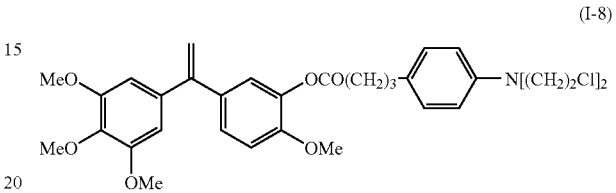

(I-8)

To a solution of the compound (I-1) (0.316 mmol) diluted in 5 mL of CH₂Cl₂ are added 0.376 mmol of 1-ethyl-3-(3'-dimethylaminopropyl)carbodiimide (EDCI), 0.347 mmol of DMAP and 0.347 mmol of chlorambucil. After 1 hour of stirring at room temperature, the reaction mixture is hydrolyzed with an aqueous saturated NaHCO₃ solution and extracted with ethyl acetate (3×3 mL). The organic phases are collected, dried on sodium sulfate and concentrated in order to obtain a residue which is purified on silica gel. Yield 70%.

H¹ NMR: δ ppm, CDCl₃, 300 MHz: 1.98-2.10 (m, 2H), 2.59 (t, 2H, J=7.5 Hz), 2.67 (t, 2H, J=7.2 Hz), 3.6-3.75 (m, 8H), 3.82 (s, 6H), 3.86 (s, 3H), 3.88 (s, 3H), 5.35 (d, 1H, J=1.0 Hz), 5.40 (d, 1H, J=1.0 Hz), 6.56 (s, 2H), 6.68 (d, 2H, J=8.7 Hz), 6.94 (d, 1H, J=8.7 Hz), 7.03 (d, 1H, J=2.4 Hz), 7.12 (d, 2H, J=8.7 Hz), 7.25 (dd, 1H, J=8.7 Hz, J=2.1 Hz). Mass spectroscopy (ESI) [M+Na]⁺=624. Elemental analysis: (MM=601.20) Calculated C, 63.79; H, 6.19. Found C, 63.68; H, 6.16.

1.10. Compound of Formula (I-9)

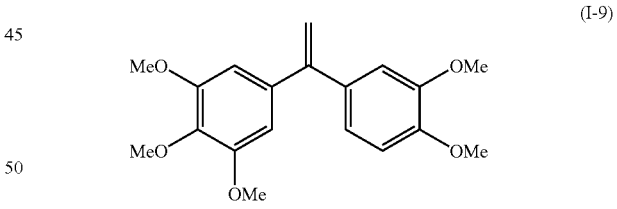

(I-9)

To a solution of the compound (I-1) (0.158 mmol) diluted in 5 mL of acetone are added 0.632 mmol of K₂CO₃ and 0.632 mmol of dimethyl sulfate. After 12 hours of stirring at room temperature, the reaction medium is hydrolyzed with an aqueous solution and extracted with ethyl acetate (3×3 mL). The organic phases are collected, dried on sodium sulfate and concentrated in order to obtain a residue which is purified on silica gel. Yield 80%.

H¹ NMR: δ ppm, CDCl₃, 300 MHz: 3.80 (s, 6H), 3.84 (s, 3H), 3.87 (s, 3H), 3.89 (s, 3H), 5.33 (d, 1H, J=1.5 Hz), 5.36 (d, 1H, J=1.5 Hz), 6.56 (s, 2H), 6.83 (d, 1H, J=8.4 Hz), 6.88-6.92 (m, 2H). Mass spectroscopy (ESI) [M+Na]⁺=353. Elemental analysis: (MM=330.15) Calculated C, 69.07; H, 6.71. Found C, 68.85; H, 6.56.

1.11. Compound of Formula (I-12)

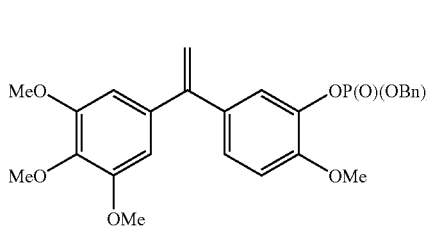

The compound (I-1) (0.136 mmol) is diluted in a mixture consisting of 153 μL of carbon tetrachloride and 1.3 mL of dry acetonitrile at −25° C. After 10 minutes of stirring, diisopropylethylamine (0.663 mmol) dimethylaminopyridine (0.0136 mmol) and dibenzylphosphite (0.458 mmol) are successively added to the reaction medium. After 1 hour 30 min of stirring at −25° C., the reaction mixture is hydrolyzed with an aqueous saturated $KH_2PO_4$ solution and extracted with ethyl acetate (3×3 mL). The organic phases are collected, dried on sodium sulfate and concentrated in order to obtain a residue which is purified on silica gel. Yield 40%.

$H^1$ NMR: δ ppm, $CDCl_3$, 300 MHz: 3.81 (s, 6H), 3.82 (s, 3H), 3.88 (s, 3H), 5.17 (d, 4H, J=7.8 Hz), 5.32 (s, 1H), 5.33 (d, 1H, J=0.6 Hz), 6.55 (s, 2H), 6.89 (d, 1H, J=8.4 Hz), 7.14 (m, 1H), 7.23 (t, 1H, J=7.3 Hz), 7.23-7.4 (m, 10H). Mass spectroscopy (ESI) $[M+Na]^+$=599. Elemental analysis: (MM=576.19) Calculated C, 66.66; H, 5.77. Found C, 66.58; H, 5.72.

1.12. Compound of Formula (I-11)

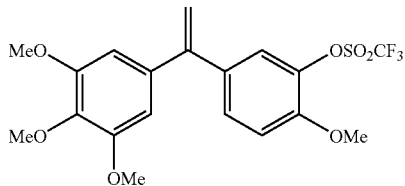

To a solution of the compound (I-1) (0.78 mmol) in 5 mL of $CH_2Cl_2$ are successively added at −10° C.: 3.11 mmol of pyridine and 1.17 mmol of triflic anhydride diluted in 5 mL of $CH_2Cl$. The whole is stirred for 1 hour at room temperature before being hydrolyzed by a 1M solution of hydrochloric acid (5 mL). The organic phase is separated and the aqueous phase is extracted with $CH_2Cl_2$ (2×10 mL). The organic phases are collected, dried on sodium sulfate, and concentrated in order to obtain a residue which is purified on silica gel. Yield 90%.

$H^1$ NMR: δ ppm, $CDCl_3$, 300 MHz: 3.84 (s, 6H), 3.90 (s, 3H), 3.96 (s, 3H), 5.42 (m, 2H), 6.54 (s, 2H), 7.02 (d, 1H, J=8.4 Hz), 7.24 (d, 1H, J=2.2 Hz), 7.36 (dd, 1H, J=8.4 Hz, J=2.2 Hz). Elemental analysis: (MM=448.08) Calculated C, 50.89; H, 4.27. Found C, 50.78; H, 4.21.

1.13. Compound of Formula (I-15)

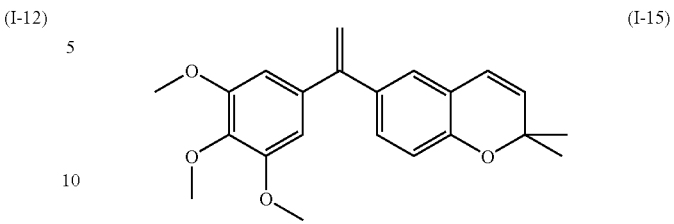

This compound was prepared according to the operating procedure described for the compound of formula (I-2) from the lithiated derivative prepared from 6-iodo-2,2-dimethyl-2H-chromene. Yield 37%.

$H^1$ NMR: δ ppm, $CDCl_3$, 300 MHz: 1.43 (s, 6H), 3.82 (s, 6H), 3.88 (s, 3H), 5.29 (d, 1H, J=1.2 Hz), 5.36 (d, 1H, J=1.2 Hz), 5.62 (d, 1H, J=10.0 Hz), 6.30 (d, 1H, J=10.0 Hz), 6.65 (s, 2H), 6.73 (d, 1H, J=8.4 Hz), 6.88 (d, 1H, J=2.4 Hz), 7.11 (dd, 1H, J=8.4 Hz, J=2.4 Hz). Elemental analyses: (MM=352.17) Calculated C, 74.98; H, 6.86. Found C, 74.11; H, 6.94.

1.14. Compound of Formula (I-16)

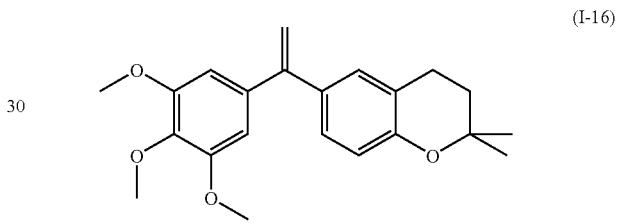

This compound was prepared according to the same procedure described for the compound of formula (I-2) from the lithiated derivative prepared from 6-iodo-2,2-dimethyl-2H-chromane. Yield 32%.

$H^1$ NMR: δ ppm, $CDCl_3$, 300 MHz: 1.35 (s, 6H), 1.88 (t, 2H, J=6.6 Hz), 2.76 (t, 2H, J=6.6 Hz), 3.82 (s, 6H), 3.88 (s, 3H), 5.26 (d, 1H, J=1.2 Hz), 5.35 (d, 1H, J=1.2 Hz), 6.57 (s, 2H), 6.74 (d, 1H, J=8.1 Hz), 7.08 (s, 1H), 7.09 (d, 1H, J=8.1 Hz). Elemental analyses: (MM=354.18) Calculated C, 74.55; H, 7.39. Found C, 74.50; H, 7.36.

1.5. Compound of Formula (I-17)

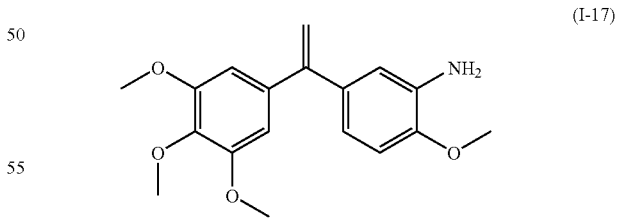

Under an inert atmosphere, at −40° C., to a solution consisting of 560 mg of (3-amino-4-methoxy)acetophenone (3.39 mmol, 1 eq.) in 20 mL of tetrahydrofurane (THF), are added dropwise 11.9 mL of a molar solution of 3,4,5-trimethoxyphenyl-magnesium bromide (3.5 eq.). The reaction medium is stirred at room temperature for 3 hours and then overnight at room temperature in order to be then hydrolyzed with a saturated ammonium chloride solution. The reaction medium is extracted three times with ethyl acetate (3×30 mL). The collected organic phases are washed with a saturated sodium chloride solution, dried on sodium sulfate, filtered and concentrated in vacuo. The residue is chromatographed on silica gel (cyclohexane/ethylacetate: 6/4), in order to lead to the intermediate secondary alcohol. The latter is then put into solution with a few grains of para-toluenesulfonic acid (APTS) in 20 mL of dichloromethane, under stirring, at room temperature for 30 minutes. After adding 20 mL of water, the reaction medium is extracted three times with dichloromethane (3×20 mL). The collected organic phases are dried on magnesium sulfate, filtered and concentrated in vacuo. The residue is chromatographed on silica gel. Yield 12%.

$H^1$ NMR: δ ppm, $CD_3COCD_3$, 200 MHz: 3.80 (s, 3H), 3.64 (s, 6H), 3.70 (s, 3H), 4.38 (s, 2H), 5.26 (d, 1H, J=1.6 Hz), 5.29 (d, 1H, J=1.6 Hz), 6.61 (s, 2H), 6.61 (dd, 1H, J=8.4 Hz, J=2.2 Hz), 6.71 (d, 1H, J=2.2 Hz), 6.79 (d, 1H, J=8.4 Hz). Elemental analyses: (MM=315.15) Calculated C, 68.55; H, 6.71; N, 4.44. Found C, 68.50; H, 6.67; N, 4.38.

1.16. Compound of Formula (I-18)

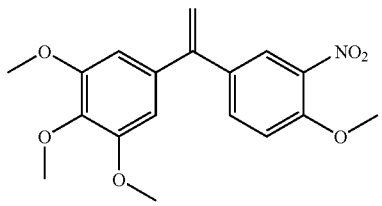

(I-18)

Under an inert atmosphere, 1.07 g of methyl triphenylphosphonium bromide (3 mmol, 1 eq.) is diluted in 10 mL of THF. Next, 2.83 mL of a molar solution of lithium hexamethyl-disilazide (LiHMDS) in THF (3 mmol) are slowly added dropwise at 0° C. The reaction medium is stirred at 0° C. for 1 hour. The solution takes an intense yellow color. Next, a solution of 520 mg of diarylketone (1.5 mmol) in 10 mL of THF is added dropwise at 0° C. The mixture is left under stirring for 30 minutes under an inert atmosphere at 0° C. and then at room temperature. 1 mL of water is added to the medium and the medium is then concentrated in vacuo. The residue is dissolved in 20 mL of dichloromethane and then washed three times with water. The organic phase is dried on $MgSO_4$ and then condensed in vacuo. The residue is chromatographed on silica gel. Yield 70%.

$H^1$ NMR: δ ppm, $CDCl_3$, 300 MHz: 3.77 (s, 6H), 3.83 (s, 3H), 3.89 (s, 3H), 6.44 (s, 2H), 7.14 (dd, 1H, J=8.4 Hz, J=2.7 Hz), 7.34 (d, 1H, J=8.4 Hz), 7.42 (d, 1H, J=2.7 Hz). Mass spectroscopy (ESI) $[M+Na]^+$=368.

1.17. Compound of Formula (I-19)

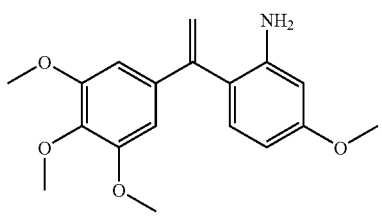

(I-19)

86 mg of compound (I-18) (0.25 mmol, 1 eq.) are dissolved in 5 mL of glacial acetic acid. After addition of 98 mg of zinc (1.5 mmol, 6 eq.), the reaction medium is left under stirring at room temperature for 1 hour. After filtration on celite and then condensation in vacuo, the residue is taken up into 15 mL of ethyl acetate and then washed three times with water. The organic phase is dried on $MgSO_4$ and then condensed in vacuo. The residue is chromatographed on silica gel. Yield 46%.

$H^1$ NMR: δ ppm, $CDCl_3$, 300 MHz: 3.79 (s, 3H), 3.80 (s, 6H), 3.85 (s, 3H), 5.28 (d, 1H, J=1.5 Hz), 5.65 (d, 1H, J=1.5 Hz), 6.24 (d, 1H, J=2.7 Hz), 6.59 (s, 2H), 7.43 (dd, 1H, J=8.4 Hz, J=2.7 Hz), 7.03 (d, 1H, J=8.4 Hz). Mass spectroscopy (ESI) $[M+Na]^+$=338.

1.18. Compound of Formula (I-20)

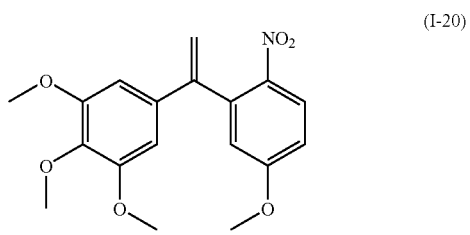

(I-20)

This compound was prepared according to the operating procedure described for the compound of formula (I-18) from the corresponding diarylketone. Yield 54%.

$H^1$ NMR: δ ppm, $CDCl_3$, 300 MHz: 3.79 (s, 3H), 3.77 (s, 6H), 3.83 (s, 3H), 3.92 (s, 3H), 6.45 (s, 2H), 6.91 (d, 1H, J=3.0 Hz), 6.96 (dd, 1H, J=9.0 Hz, J=3.0 Hz), 8.05 (d, 1H, J=9.0 Hz). Mass spectroscopy (ESI) $[M+Na]^+$=368.

1.19. Compound of Formula (I-21)

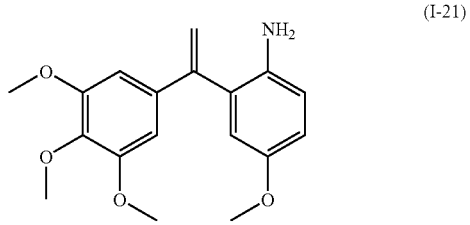

(I-21)

This compound was prepared according to the operating procedure described for the compound of formula (I-19) from the corresponding diarylketone. Yield 70%.

$H^1$ NMR: δ ppm, $CDCl_3$, 300 MHz: 3.77 (s, 3H), 3.80 (s, 6H), 3.85 (s, 3H), 3.92 (s, 3H), 5.32 (d, 1H, J=1.5 Hz), 5.71 (d, 1H, J=1.5 Hz), 6.59 (s, 2H), 6.66 (d, 1H, J=8.4 Hz), 6.72-6.79 (m, 2H). Mass spectroscopy (ESI) $[M+Na]^+$=338.

1.20. Compound of Formula (I-22)

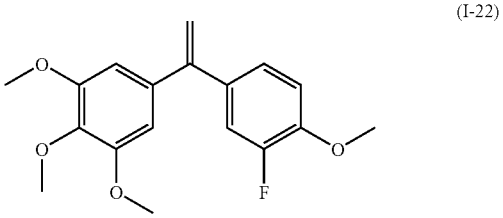

(I-22)

This compound was prepared according to the operating procedure described for the compound of formula (I-5) from 3,4,5-trimethoxyacetophenone and from 2-fluoro-4-iodoanisole. Yield 48%.

H¹ NMR: δ ppm, CDCl₃, 300 MHz: 3.82 (s, 6H), 3.88 (s, 3H), 3.92 (s, 3H), 3.92 (s, 3H), 5.35 (d, 1H, J=1.5 Hz), 5.38 (d, 1H, J=1.5 Hz), 6.58 (s, 2H), 6.95 (m, 1H), 7.05-7.19 (m, 2H). Mass spectroscopy (ESI) [M+Na]⁺=341.

1.21. Compound of Formula (I-23)

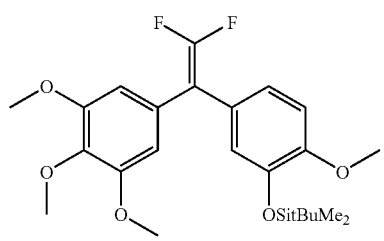
(I-23)

This compound was prepared according to the operating procedure described for the compound of formula (I-18) from the corresponding diarylketone. Yield 60%.

H¹ NMR: δ ppm, CDCl₃, 300 MHz: 0.00 (s, 6H), 0.83 (s, 9H), 3.70 (s, 6H), 3.72 (s, 3H), 3.76 (s, 3H), 6.40 (s, 2H), 6.68 (s, 1H), 6.72 (s, 2H). Elemental analyses: (MM=466.20) Calculated C, 61.78; H, 6.91. Found C, 66.70; H, 6.84.

1.22. Compound of Formula (I-24)

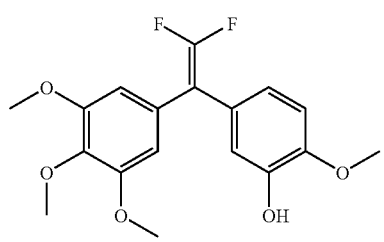
(I-24)

This compound was prepared according to the operating procedure described for the compound of formula (I-1) from (I-23). Yield 89%.

H¹ NMR: δ ppm, CDCl₃, 300 MHz: 3.85 (s, 6H), 3.92 (s, 3H), 3.99 (s, 3H), 5.68 (s, 1H), 6.50 (s, 2H), 6.80-6.98 (m, 3H). Mass spectroscopy (ESI) [M+Na]⁺=375.2.

1.23. Compound of Formula (I-25)

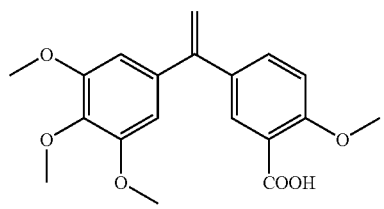
(I-25)

At −78° C., 0.85 mL of BuLi (1.6 M) is slowly introduced into a flask containing 400 mg of (I-13) in 10 mL of diethylether. The whole is reacted for 1 hour 30 min at −70° C. and then 2 g of CO₂ as dry ice are added to the reaction medium at −78° C. After 30 minutes of stirring at −78° C., the solution is left to warm up to room temperature. The raw reaction product is hydrolyzed with a saturated NH₄Cl solution and is extracted with diethylether (10 mL). The organic phase is treated with a soda solution (1M; 10 mL) and after decantation, the aqueous phase is taken up with a HCl 1M solution (15 mL). After extraction with diethylether (3×10 mL), the collected organic phases are washed with a saturated sodium chloride solution, dried on sodium sulfate, filtered and concentrated in vacuo and the residue is chromatographed on silica gel. Yield 44%.

H¹ NMR: δ ppm, CDCl₃, 300 MHz: 3.68 (s, 3H), 3.71 (s, 6H), 3.76 (s, 3H), 5.25 (m, 1H), 5.64 (m, 1H), 6.42 (s, 2H), 6.88 (d, 1H, J=8.6 Hz), 7.94 (d, 1H, J=2.2 Hz), 8.05 (dd, 1H, J=8.6 Hz, J=2.2 Hz). Elemental analyses: (MM=344.13) Calculated C, 66.27; H, 5.85. Found C, 66.19; H, 5.80.

1.24. Compound of Formula (I-26)

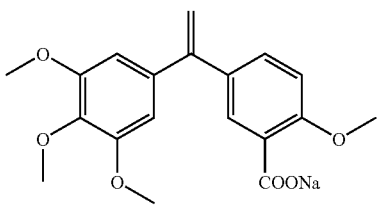
(I-26)

344 mg of (I-25) and 40 mg of NaOH are dissolved in 5 mL of MeOH. After total dissolution, the medium is concentrated on the rotary evaporator and then in vacuo from a vane pump. Yield 100%.

H¹ NMR: δ ppm, D₂O, 300 MHz: 3.72 (s, 12H), 5.32 (s, 1H), 5.79 (s, 1H), 6.60 (s, 2H), 7.08 (d, 1H, J=8.8 Hz), 7.80 (m, 1H), 7.90 (m, 1H). Elemental analyses: (MM=366.11) Calculated C, 62.29; H, 5.23. Found C, 62.07; H, 5.12.

1.25. Compound of Formula (I-27)

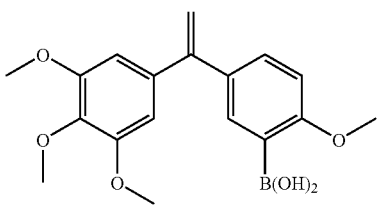
(I-27)

At −78° C., 0.56 mL of BuLi (1.6 M) are slowly introduced into a flask containing 342 mg of (I-13) in 5 mL of THF. The whole is reacted for 30 minutes at −70° C. and the raw reaction product is mixed at room temperature until complete dissolution and then the whole is again cooled down to −78° C. 0.21 g of triisopropyl borate is slowly added to the reaction medium at −78° C. and the solution is slowly brought back to room temperature. After 10 minutes of stirring, 5 mL of H₂O are added to the raw reaction product followed by 20 mL of ether and 15 mL of a saturated NH₄Cl solution. After extraction, the collected organic phases are dried on sodium sulfate, filtered and concentrated in vacuo. Yield 89%.

H¹ NMR: δ, ppm, CDCl₃, 300 MHz: 3.80 (s, 3H), 3.84 (s, 6H), 3.91 (s, 3H), 5.40 (d, 1H, J=1.5 Hz), 5.80 (d, 1H, J=1.5 Hz), 6.58 (s, 2H), 7.02 (d, 1H, J=7.8 Hz), 8.10 (d, 1H, J=2.2 Hz), 8.28 (dd, 1H, J=7.8 Hz, J=2.2 Hz).

1.26. Compound of Formula (I-28)

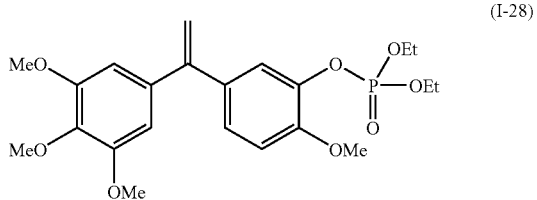

To a solution of the compound (I-1) (1.15 mmol) in 8 mL of dry THF, are added dropwise 850 μL of a pyridine/diisopropylethylamine mixture (5:1) and 5.17 mmol of diethoxyphosphate chloride. After one night of stirring at room temperature, the reaction mixture is hydrolyzed and extracted with ethyl acetate (3×2 mL). The organic phases are collected, dried on sodium sulfate, filtered, and the solvent is evaporated and the residue is chromatographed on silica gel. Yield 79%.

$H^1$ NMR $CDCl_2$, 300 MHz δ ppm: 1.23 (td, 9H, $J_1$=7 Hz, $J_2$=1 Hz), 3.72 (s, 6H), 3.76 (s, 3H), 3.78 (s, 3H), 4.13 (qd, 8H, $J_1$=8.4 Hz, $J_2$=1.5 Hz), 5.25 (d, 1H, J=1.2 Hz), 5.29 (d, 1H, J=1.2 Hz), 6.46 (s, 2H), 6.82 (d, 1H, J=8.7 Hz), 7.05 (m, 1H); 7.17 (t, 1H, J=1.8 Hz). Mass spectroscopy (APCI) $[M+H]^+$ =453.

1.27. Compound of Formula (I-29)

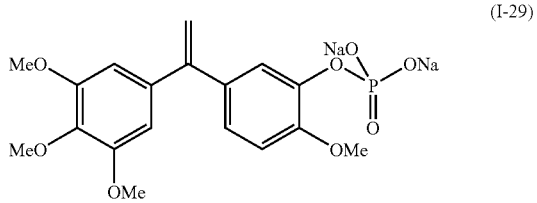

To a solution of the compound (I-28) (0.126 mmol) in 1 mL of dry $CH_2Cl_2$, are added dropwise at 0° C., 0.252 mL of trimethylsilane iodide. After one hour of stirring at room temperature, the reaction mixture is hydrolyzed and extracted with ethyl acetate (2×3 mL). The organic phases are collected, washed with a saturated sodium thiosulfate solution, dried on sodium sulfate, filtered and the solvent is evaporated. The raw product (23.2 mg) is taken up in a solution of 0.25 mmol of sodium methanoate and the raw product is left for one further hour at room temperature. The solvent is then evaporated and the raw product is taken up into ether, filtered on sintered glass and washed with ether. The expected compound (very hygroscopic) is obtained as a yellow powder. Yield 41%.

Elemental analyses: (MM=440.06) Calculated C, 49.10; H, 4.35. Found C, 48.67; H, 4.00.

1.28. Compound of Formula (I-30)

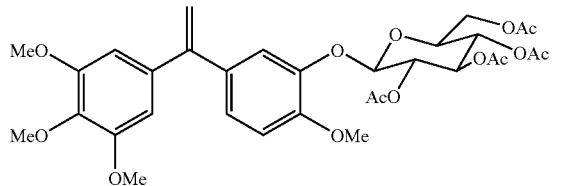

To a solution of the compound (I-1) (0.316 mmol) in 5 mL of dry acetonitrile is added 1.15 mmol of potash. The mixture is stirred for 20 min and then a solution of tetraacetylated α-bromo-glucopyranose (0.632 mmol) in 5 mL of acetonitrile is added drop wise. After one night of stirring, the reaction mixture is hydrolyzed with a 1N HCl solution (5 mL) and extracted with ethyl acetate (3×5 mL). The organic phases are collected, dried on sodium sulfate, filtered and the solvent is evaporated and the residue is chromatographed on silica gel. Yield 25%, 50% of the starting product being unreacted.

$^1$H NMR $CDCl_3$, 300 MHz δ ppm: 2.01 (s, 3H), 2.02 (s, 6H), 2.05 (s, 3H), 3.80 (s, 6H), 3.83 (s, 3H), 3.86 (s, 3H), 4.04-4.16 (m, 2H), 4.24 (dd, 1H, J=12 Hz, J=5.1 Hz), 4.99 (m, 1H), 5.13 (m, 1H), 5.24-5.30 (m, 2H), 5.31 (s, 1H), 5.35 (s, 1H), 6.52 (s, 2H), 6.83 (d, 1H, J=8.4 Hz), 7.00 (dd, 1H, J=8.4 Hz, J=2.1 Hz), 7.18 (d, 1H, J=2.4 Hz). Mass spectroscopy (ESI) $[M+Na]^+$=669.7.

1.29. Compound of Formula (I-31)

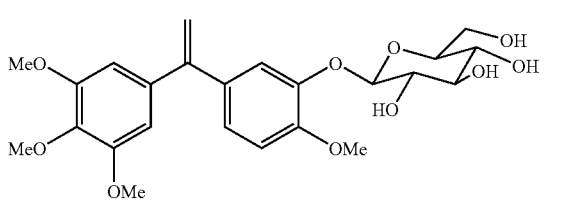

To a solution of the compound (I-30) (0.078 mmol) in 2 mL of dry methanol, are added 8 mL of a 28% ammonia solution. After 2 hours of stirring at 60° C., the reaction medium is hydrolyzed with an HCl 1N solution, and extracted with ethyl acetate (3×5 mL). The organic phases are collected, dried on sodium sulfate, filtered and the solvent is evaporated and the residue is chromatographed on silica gel. Yield 90%.

$H^1$ NMR $CDCl_3$, 300 MHz δ ppm: 3.10-3.50 (m, 5H), 3.52 (d, 1H, J=11.7 Hz), 3.68 (s, 6H), 3.73 (s, 6H), 3.78 (s, 3H), 4.48 (s, 1H), 4.86 (m, 1H), 4.94 (s, 1H), 5.03 (s, 1H), 5.18 (s, 1H), 5.34 (m, 1H), 5.45 (s, 1H), 6.55 (s, 2H), 6.86 (dd, 1H, J=7.8 Hz, J=1.5 Hz), 6.96 (d, 1H, J=8.4 Hz), 7.12 (d, 1H, J=1.5 Hz). Mass spectroscopy (ESI) $[M+Na]^+$=501.

1.30. Compound of Formula (I-32)

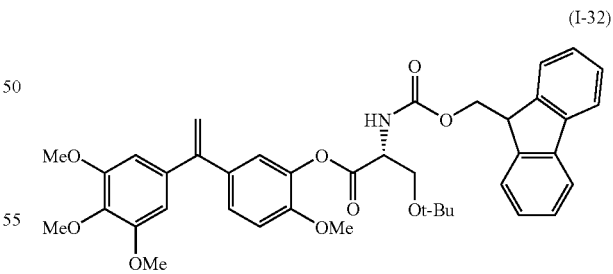

To a solution of the compound (I-1) (0.79 mmol) in 15 mL of $CH_2Cl_2$, are added 0.94 mmol of 1-ethyl-3-(3-dimethylamino-propyl)carbodiimide hydrochloride (EDCI), 0.87 mmol of N,N-4-dimethylaminopyridine (DMAP) and 0.87 mmol of N-Fmoc serine (Ot-Bu) (serine, the amine function of which is protected by a 9-fluorenylmethoxycarbonyl group (Fmoc) and the acid function of which is protected by a tert-butyl group). After one night of stirring, the reaction medium is hydrolyzed with an aqueous saturated $NaHCO_3$ solution, and extracted with ethyl acetate (3×10 mL). The organic phases are collected, dried on sodium sulfate, filtered, and the solvent is evaporated and the residue is chromatographed on silica gel. Yield 39%.

H$^1$ NMR CDCl$_3$, 300 MHz δ ppm: 1.09 (s, 9H), 3.64 (dd, 1H, J=9.0 Hz, J=2.7 Hz), 3.73 (s, 6H), 3.76 (s, 3H), 3.79 (s, 3H), 3.95 (dd, 1H, J=9.0 Hz, J=3.0 Hz), 4.19 (t, 1H, J=6.9 Hz), 4.27-4.39 (m, 2H), 4.72 (m, 1H), 5.26 (s, 1H), 5.31 (s, 1H), 6.67 (d, 1H, J=9.0 Hz), 6.47 (s, 2H), 6.87 (d, 1H, J=8.7 Hz), 6.98 (d, 1H, J=2.1 Hz), 7.18 (dd, 1H, J=8.4 Hz, J=2.4 Hz), 7.23 (d, 2H, J=7.5 Hz), 7.31 (t, 2H, J=7.2 Hz), 7.53 (m, 2H), 7.68 (d, 2H, J=7.2 Hz). Mass spectroscopy (ESI) [M+Na]$^+$=704.

1.31. Compound of Formula (I-33)

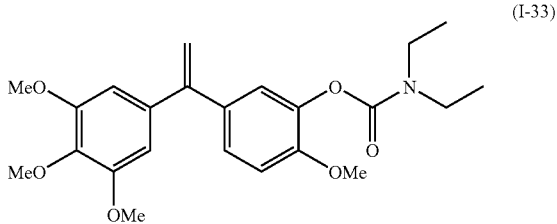

(I-33)

To a solution of the compound (I-1) (0.316 mmol) in 2 mL of dry CH$_2$Cl$_2$, are added 54 µL of pyridine and 0.632 mmol of N,N-diethylcarbamic acid chloride. After one night of stirring at room temperature, the reaction mixture is hydrolyzed and extracted with ethyl acetate (3×3 mL). The organic phases are collected, dried on sodium sulfate, filtered, and the solvent is evaporated and the residue is chromatographed on silica gel. Yield 50%.

H$^1$ NMR CDCl$_3$, 300 MHz δ ppm: 1.11-1.20 (m, 6H), 3.28-3.39 (m, 4H), 3.75 (s, 6H), 3.77 (s, 3H), 3.80 (s, 3H), 5.25 (d, 1H, J=0.9 Hz), 5.32 (d, 1H, J=1.2 Hz), 6.50 (s, 2H); 6.82 (d, 1H, J=8.4 Hz), 7.05-7.10 (m, 2H). Mass spectroscopy (ESI) [M+Na]$^+$=438.

1.32. Compound of Formula (I-34)

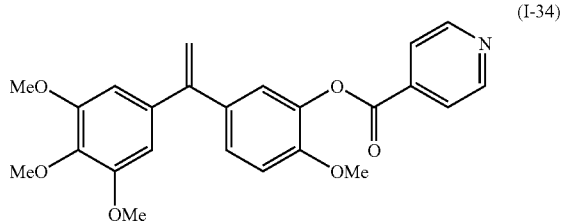

(I-34)

To a solution of the compound (I-1) (0.316 mmol) in 5 mL of CH$_2$Cl$_2$, are added 0.47 mmol of EDCI, 0.47 mmol of DMAP and 0.47 mmol of isonicotinic acid. After one night of stirring at room temperature, the reaction mixture is hydrolyzed with an aqueous saturated NaHOCO$_3$ solution (3 mL) and extracted with ethyl acetate (3×3 mL). The organic phases are collected, dried on sodium sulfate, filtered and the solvent is evaporated, and the residue is chromatographed on silica gel. Yield 85%.

$^1$H NMR CDCl$_3$, 300 MHz δ ppm: 3.74 (s, 6H), 3.76 (s, 3H), 3.79 (s, 3H), 5.28 (d, 1H, J=0.9 Hz), 5.34 (d, 1H, J=1.2 Hz), 6.49 (s, 2H), 6.91 (d, 1H, J=8.4 Hz), 7.10 (d, 1H, J=2.1 Hz), 7.22 (dd, 1H, J=8.4 Hz, J=2.1 Hz), 7.92 (dd, 1H, J=4.8 Hz, J=1.8 Hz), 8.76 (d, 1H, J=4.8 Hz). Mass spectroscopy (ESI) [M+Na]$^+$=444.

1.33. Compound of Formula (I-35)

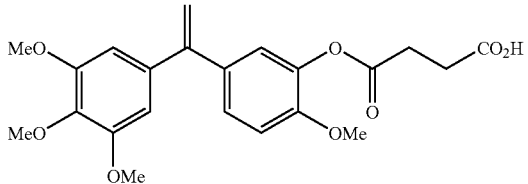

(I-35)

To a solution of the compound (I-1) (0.316 mmol) in 5 mL of pyridine are added 0.47 mmol of succinic anhydride and 0.06 mmol of DMAP. After one night of stirring, the reaction mixture is hydrolyzed with 5 mL of an aqueous saturated NaHCO$_3$ solution, and extracted with ethyl acetate (3×3 mL). The organic phases are collected, dried on sodium sulfate, filtered and the solvent evaporated, and the residue is chromatographed on silica gel. Yield 55%.

$^1$H NMR CDCl$_3$, 300 MHz δ ppm: 2.73 (td, 2H, J=6.3 Hz, J=1.5 Hz), 2.84 (td, 2H, J=6.9 Hz, J=1.5 Hz), 3.74 (s, 6H), 3.76 (s, 3H), 3.80 (s, 3H), 5.27 (d, 1H, J=0.9 Hz), 5.32 (d, 1H, J=0.9 Hz), 6.48 (s, 2H), 6.85 (d, 1H, J=8.7 Hz), 6.98 (d, 1H, J=2.1 Hz), 7.15 (dd, 1H, J=8.7 Hz, J=2.1 Hz). Mass spectroscopy (ESI) [M+Na]$^+$=439.

1.34. Compound of Formula (I-36)

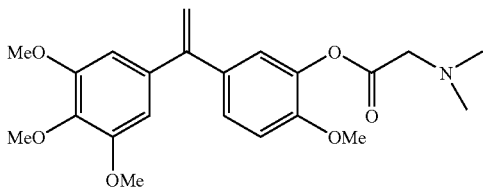

(I-36)

To a solution of the compound (I-1) (0.316 mmol) in 5 mL of CH$_2$Cl$_2$, are added 0.47 mmol of EDCI, 0.47 mmol of DMAP and 0.47 mmol of N,N-dimethylglycine. After one night of stirring at room temperature, the reaction medium is hydrolyzed with 6 mL of an aqueous saturated NaHCO$_3$ solution, and extracted with ethyl acetate (3×3 mL). The organic phases are collected, dried on sodium sulfate, filtered and the solvent is evaporated, and the residue is chromatographed on silica gel. Yield 65%.

$^1$H NMR CDCl$_3$, 300 MHz δ ppm: 2.37 (s, 6H), 3.37 (s, 2H); 3.74 (s, 6H), 3.77 (s, 3H), 3.80 (s, 3H), 5.26 (s, 1H), 5.31 (s, 1H), 6.47 (s, 2H), 6.86 (d, 1H, J=8.7 Hz), 6.97 (d, 1H, J=2.1 Hz), 7.16 (dd, 1H, J=8.4 Hz, J=2.1 Hz). Mass spectroscopy (ESI) [M+Na]$^+$=424.

1.35. Compound of Formula (I-37)

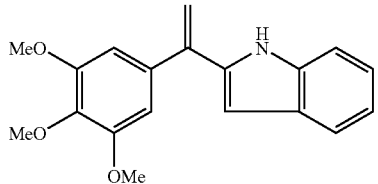

(I-37)

To a solution of indole (165 mg, 1.41 mmol) in 5 mL of anhydrous THF, are successively added 1.83 mmol of trimethoxyacetophenone and 0.14 mmol of TiCl$_4$. The mixture is stirred under nitrogen at room temperature for 2 hours. 100 mL of water are added into the reaction medium and a white suspension is formed, which is filtered on a frit in order to deliver 150 mg of white powder. The filtrate is extracted with 3×30 mL of dichloromethane. The aqueous phase is then alkalinized with a saturated sodium carbonate solution up to a pH=10 and is extracted again with 3×30 mL of dichloromethane. The organic phase is washed with a saturated sodium carbonate solution, and then is dried on sodium sulfate, filtered and concentrated under reduced pressure in order to provide 415 mg of raw product which is dissolved in 5 mL of dichloromethane and 0.68 mmol of APTS are added. The mixture is stirred under nitrogen at room temperature for 30 minutes. 100 mL of a saturated sodium carbonate solution are added, and the solution is extracted with 3×30 mL of dichloromethane. The organic phase is dried on sodium sulfate, filtered and concentrated under reduced pressure in order to provide 110 mg of raw product which is purified on a silica column. Yield=70%.

$^1$H NMR 300 MHz; CDCl$_3$, δ (ppm): 1.45 (m, 1H), 1.49 (m, 1H), 1.81 (m, 1H), 1.96 (s, 1H), 2.22 (m, 1H), 2.42 (td, 1H, J=11.0 Hz, J=4.0 Hz), 2.67 (m, 1H), 2.82 (m, 1H), 3.01 (dd, 1H, J=16 Hz, J=9.0 Hz), 3.23 (m, 2H), 4.36 (q, 1H, J=9.0 Hz), 7.02 (t, 1H, J=8.0 Hz), 7.21 (m, 2H), 7.58 (d, 1H, J=8.0 Hz). Mass spectroscopy (ESI) [M+Na]$^+$: 332.

1.36. Compound of Formula (I-38)

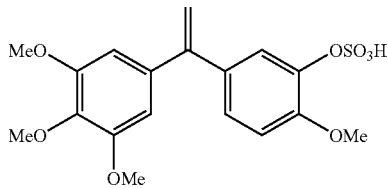

(I-38)

To a solution of the compound (I-1) (0.316 mmol) in 1 mL of anhydrous pyridine, are added 0.47 mmol of the SO$_3$/pyridine complex. After 24 hrs of stirring at 20° C., the reaction mixture is hydrolyzed with 0.5 mL of distilled water and the solvent is evaporated. And the residue is purified by chromatography on silica gel. Yield 80%.

$^1$H NMR CDCl$_3$, 300 MHz δ ppm: 3.59 (s, 3H), 3.71 (s, 6H), 3.82 (s, 3H), 5.22 (s, 1H), 5.30 (s, 1H), 6.47 (s, 2H), 6.66 (d, 1H, J=8.7 Hz), 6.95 (dd, 1H, J=8.7 Hz, J=1.8 Hz), 7.54 (d, 1H, J=1.8 Hz). Mass spectroscopy (negative ESI) [M−H]$^+$= 395.

1.37. Compound of Formula (I-39)

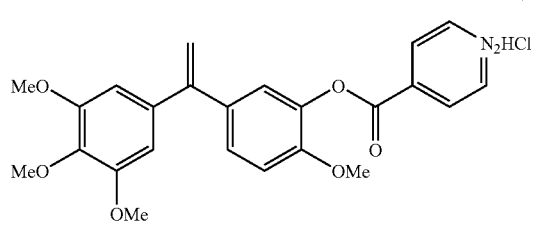

(I-39)

To a solution of 0.2 mmol of the compound (I-34) in 1 mL of anhydrous methanol, is added 1 mL of a saturated HCl/MeOH solution. After 12 hrs of stirring at room temperature, the solvent is evaporated and the raw product is taken up in ether, filtered on sintered glass and washed with ether. The compound (I-39) is obtained as a yellow powder. Yield 89%.

Elemental analyses: (MM=453.13) Calculated C, 63.00; H, 5.25; N, 3.06. Found C, 62.87; H, 5.12; N, 2.91.

1.38. Compound of Formula (I-40)

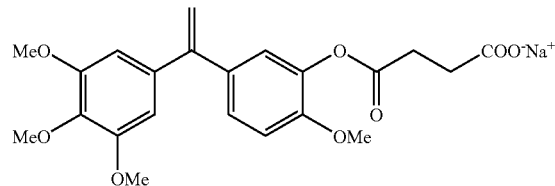

(I-40)

To a solution of 0.1 mmol of the compound (I-35) in 1 mL of methanol, is added 0.1 mml of soda. The mixture is stirred for 30 minutes. The solvent is then evaporated and the raw product taken up in ether, filtered on sintered glass and washed with ether. The expected compound is obtained as a white powder. Yield 83%.

Elemental analyses: (MM=438.13) Calculated C, 60.27; H, 5.29. Found C, 60.20; H, 5.23.

1.39. Compound of Formula (I-41)

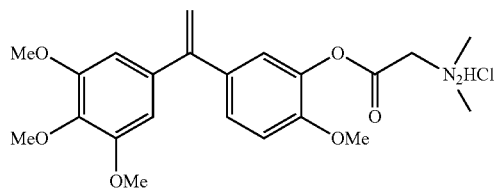

(I-41)

To a solution of 0.2 mmol of the compound (I-36) in 1 mL of anhydrous methanol, is added 1 mL of a saturated HCl/MeOH solution. After 12 h of stirring at room temperature, the solvent is evaporated and the raw product is taken up in ether, filtered on sintered glass and washed with ether. The compound (I-41) is obtained as a white powder. Yield 68%.

Elemental analyses: (MM=437.16) Calculated C, 60.34; H, 6.44; N, 3.20. Found C, 60.21; H, 6.34; N, 3.11.

1.40. Compound of Formula (I-42)

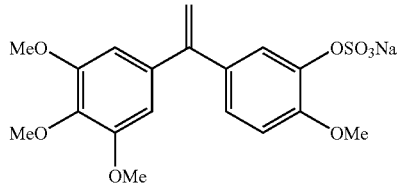

(I-42)

To a solution of 0.05 mmol of the compound (I-38) in 1 mL of anhydrous methanol, are added at 0° C., 0.1 mmol of sodium methanoate. The mixture is stirred under nitrogen at room temperature for 30 minutes. The solvent is then evaporated and the raw product is taken up in ether, filtered on sintered glass and washed with ether. The expected compound is obtained as a white powder. Yield 69%.

Elemental analyses: (MM=418.07) Calculated C, 51.67; H, 4.58; N, 3.20. Found C, 51.60; H, 4.52.

1.41. Compound of Formula (I-43)

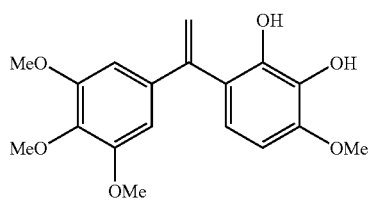

At −78° C., 1 mmol of tBuLi (2 eq.) is added to a solution containing 1.5 mmol of 5-iodo-1,2,3-trimethoxybenzene dissolved in 2 mL of distilled toluene. After 45 minutes of stirring at this temperature, 1 mmol of 1-(2,3-dihydroxy-4-methoxy-phenyl)ethanone diluted in 5 mL of distilled toluene is added. This mixture is stirred for 2 hours while letting the temperature rise up gradually and it is then slowly hydrolyzed by a saturated NH$_4$Cl solution up to a pH=7-8. After extraction with ethyl acetate (3×20 mL), the collected organic phases are dried on Na$_2$SO$_4$ and concentrated in the rotary evaporator. The raw reaction product is taken up in 2 mL of CH$_2$Cl$_2$ to which is added a dash of para-toluenesulfonic acid (APTS) from a spatula, and is then stirred for 3 hours at room temperature. The solution is washed with a saturated NaCl solution and extracted with CH$_2$Cl$_2$. After drying on Na$_2$SCO$_4$ and concentration in the rotary evaporator, an oil is collected which is purified by chromatography. Yield 32%.

$^1$H NMR: δ ppm, CD$_3$Cl$_3$, 300 MHz: 3.80 (s, 3H), 3.85 (s, 3H), 3.92 (s, 3H), 5.33 (s, 1H), 5.37 (d, 1H, J=1.2 Hz), 5.42 (s, 1H), 5.66 (d, 1H, J=1.2 Hz), 6.50 (d, 1H, J=8.7 Hz), 6.57 (s, 2H), 6.71 (d, 1H, J=8.7 Hz). Mass spectroscopy (ESI) (M+Na)=355.

1.42. Compound of Formula (I-44)

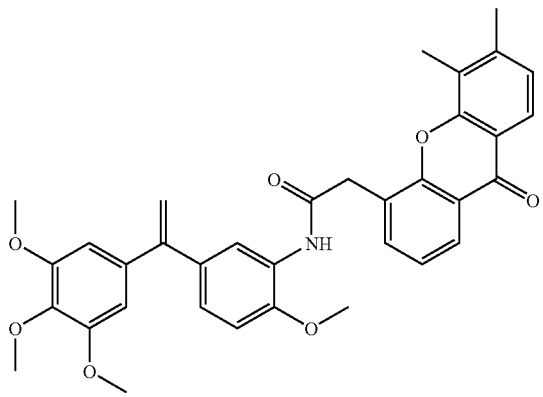

To a solution of DMXAA (220 mg, 0.78 mmol), of pyridine (65 mg, 0.811 mmol) and of (Boc)$_2$O (255 mg, 1.17 mmol) in dimethylformamide (DMF) (1.5 mL), is added the compound (I-17) (205 mg, 0.65 mmol). After 24 h of stirring at room temperature, the obtained gel is diluted in 25 mL of ethyl acetate, the organic phase is washed with a saturated NaHCO$_3$ solution, and then by a saturated 1 M KHSO$_4$ solution. The organic phase is then dried on MgSO$_4$ and concentrated, and the obtained residue is purified on a column of silica gel. Yield 10%.

$^1$H NMR: δ ppm, CD$_3$Cl$_3$, 300 MHz: 2.50 (s, 3H), 2.51 (s, 3H), 3.55 (s, 3H), 3.82 (s, 6H), 3.90 (s, 3H), 4.17 (s, 2H), 5.34 (d, 1H, J=13.2 Hz), 5.42 (d, 1H, J=13.2 Hz), 6.57 (s, 2H), 6.70 (d, 1H, J=8.4 Hz), 6.95 (m, 1H), 7.25 (d, 1H, J=8.2 Hz), 7.45 (t, 1H, J=8.2 Hz), 7.45 (d, 1H, J=8.0 Hz), 8.06 (s, 1H), 8.17 (d, 1H, J=8.1 Hz), 8.38 (d, 1H, J=7.9 Hz), 8.48 (m, 1H).

Elemental analyses: (MM=579.23) Calculated C, 72.52; H, 5.74; N, 2.42. Found C, 72.17; H, 5.55; N, 2.25.

1.43. Compound of Formula (I-45)

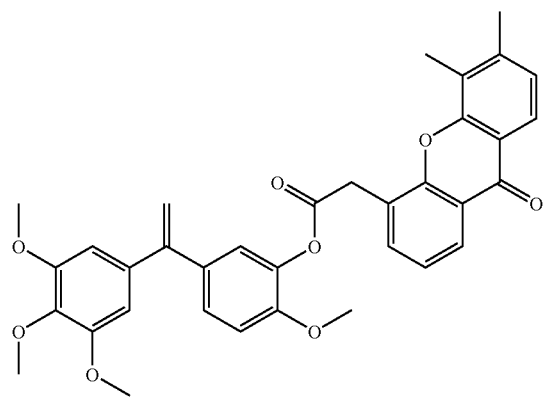

Under an inert atmosphere, to a solution of DMXAA (214 mg, 0.76 mmol, 1.2 eq.) in 3 mL of distilled DMF and 0.06 mL of distilled pyridine, is added (Boc)$_2$O (207 mg, 0.95 mmol, 1.5 eq.). After a few minutes under stirring, the derivative (I-1) (200 mg, 0.63 mmol, 1 eq.) is added to the reaction medium. After 24 hours of stirring under an inert atmosphere, the mixture is taken up with 30 mL of ethyl acetate The organic phase is washed with a saturated NaHCO$_3$ solution (3×20 mL), and then with a saturated NH$_4$Cl solution (3×20 ml), and with a saturated NaCl solution (3×20 mL), is dried on sodium sulfate, filtered on sintered glass, and then concentrated in vacuo. The residue is then purified by chromatography on a column of silica gel. Yield 34%.

$^1$H NMR: δ ppm, CD$_3$Cl$_3$, 300 MHz: 3.62 (s, 3H); 3.78 (s, 6H); 3.86 (s, 3H); 4.23 (s, 2H); 5.32 (d, 2H, J=3.8 Hz); 6.52 (s, 2H); 6.86 (d, 1H, J=8.5 Hz); 7.01 (d, 1H, J=2.2 Hz); 7.19 (m, 2H); 7.35 (t, 1H, J=7.6 Hz); 7.75 (d, 1H, J=7.6 Hz); 8.08 (d, 1H, J=8.0 Hz); 8.29 (d, 1H, J=8.0 Hz). Mass spectroscopy (ESI) (M+Na)=603.6.

1.44. Compound of Formula (I-46)

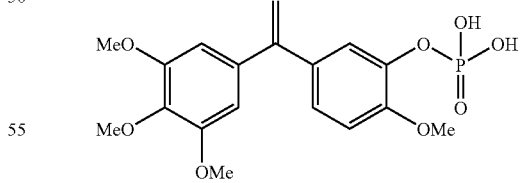

To a solution of the diethoxyphosphate compound (I-28) (0.126 mmol) in 1 mL of dry CH$_2$Cl$_2$, are added dropwise at 0° C., 0.252 mL of trimethylsilane iodide. After one hour of stirring at room temperature, the reaction mixture is hydrolyzed and extracted with ethyl acetate (3×3 mL). The organic phases are collected, washed with an aqueous saturated sodium thiosulfate solution, dried on sodium sulfate, filtered and the solvent is concentrated in order to obtain a residue which is purified on silica gel. Yield 69%.

Elemental analysis: (MM=396.33) Calculated C, 54.55; H, 5.34. Found C, 54.12; H, 5.17. Mass spectroscopy (negative APCI) (M−H)+=395

EXAMPLE 2

Biological Study In Vitro of the Compounds of the Invention

The effects on the proliferation of various cancer cells as well as on the proliferation of endothelial cells were studied.

The biological activity of the compounds of the invention was studied in vitro on 7 human cancer cell lines with different tissue origins (HCT116: colorectal carcinoma; K562: chronic myeloid leukemia; B16-F10: melanoma; U87: glioblastoma; A549: lung cancer and MDA-MB 231 and MDA-MB 435: breast cancer). The cells selected for the study were incubated at 37° C. in the presence of one of the compounds added into the culture medium at different concentrations. The whole of the conducted experiments allowed determination of the toxicity level of the tested compound, its effect on the course of the cell cycle as well as its capacity of inducing cell death by apoptosis.

2.1. Study of Cytotoxicity

The cancer cell lines originate from the American Type Culture Collection (Rockville, Md., USA) and were grown according to the recommendations of the supplier.

The cells A549, U87, MDA-MB231, MDA-MB435 and B16F10 were grown in a culture medium "Dulbecco minimal essential medium" (DMEM) containing 4.5 g/L of glucose and supplemented with 10% fetal calf serum and 1% glutamine. The K562 and HCT116 were grown in an RPMI 1640 medium containing 10% fetal calf serum and 1% glutamine. All the cell lines were maintained in the culture at 37° C. in a humid atmosphere containing 5% of $CO_2$. Cell viability was evaluated by using the reagent "CellTiter-Blue™" (Promega, Wis., USA) while observing the instructions of the manufacturer. The cells were sown in 96-well culture plates with 5000 cells per well in 50 µL of culture medium. After 24 hours of culture, the compounds of general formula (I) dissolved in DMSO were individually added into each of the wells in an amount of 50 µl per well. All the compounds were tested in triplicate for each defined concentration and each experiment was repeated three times. After 72 hours of incubation, 20 µL of resazurin were added in each well. After 2 hours of incubation, the emitted fluorescence was measured at 590 nm after excitation at 560 nm by means of a fluorescence reader of the Victor type (Perkin-Elmer, USA).

The concentration of each of the compounds which induces the death of 50% of the cells ($IC_{50}$) was determined after 72 hours of incubation. Certain compounds according to the invention have an $IC_{50}$ of the order of one nanomolar concentration, therefore equivalent to CA-4 taken as a reference. The obtained results are shown in the following Table 1.

TABLE 1

| Molecules of the invention | $IC_{50}$ for different cell lines (nM) | | | | | | |
|---|---|---|---|---|---|---|---|
| | HCT116 | K562 | B16F10 | U87 | A549 | M435 | M231 |
| (I-1) | 2-4 | 5 | 2 | 8 | 8 | 4.5 | 4 |
| (I-2) | 42 | — | — | — | 28 | 25 | 40 |
| (I-6) | 8 | — | — | 18 | 25 | 11 | 9 |
| (I-7) | 8 | — | — | 15 | 28 | 25 | 50 |
| (I-8) | 25 | — | — | 35 | 42 | 40 | 50 |

TABLE 1-continued

| Molecules of the invention | $IC_{50}$ for different cell lines (nM) | | | | | | |
|---|---|---|---|---|---|---|---|
| | HCT116 | K562 | B16F10 | U87 | A549 | M435 | M231 |
| (I-17) | — | — | — | — | 8 | — | 6 |
| (I-22) | 7 | — | — | — | — | — | — |
| (I-32) | 8 | — | — | — | — | — | — |
| (I-34) | 3 | — | — | — | — | — | — |
| (I-35) | 5 | — | — | — | — | — | — |
| (I-36) | 3 | — | — | — | — | — | — |
| (I-45) | 7 | — | — | — | — | — | — |

— means that no measurement was carried out.

2.2. Study of the Cell Cycle

The K562 and MDA-MB231 cells are sown in 6-well culture plates with 300,000 cells per well in their respective media as described above. After 24 hours of culture, the compound (I-1) was added in each of the wells at different concentrations. After 24 hours of incubation, the cells are collected individually in 15 mL tubes and then centrifuged. The cells are then washed twice in cold PBS and then resuspended in 1 mL of PBS, fixed by adding 2 mL of cold absolute ethanol and placed at 4° C. for 1 hour. After centrifugation, the cells are washed twice in PBS and then the cell pellet is taken up in 100 µL of Triton X100 at 1%. After 30 minutes of incubation at room temperature, 50 µL of RNase A boiled beforehand (1 mg/mL) and 500 µL of propidium iodide (50 µg/mL) are added into each tube and incubated in the dark at room temperature for 30 minutes. The distribution of the number of cells in each of the phases of the cell cycle is then determined by flow cytometry with a cytometer of the FC500 type (Beckman-Coulter, France).

Flow cytometry analysis of the treated cells (K562 and MDA-MB231) with the compound (I-1) has shown that the latter blocks cell division in the G2/M phase. This effect is significant after 24 hours of exposure of the cells to the compound (I-1) used at a concentration of 5 nM (FIG. 1).

2.3. Study of Apoptosis

In order to specify whether the compound (I-1) causes cell death by apoptosis, the intracellular enzymatic activity of caspases 3 and 7 was evaluated in cultures of K562, HCT116 and MDA-MB 231 cells exposed for 24 hours to the action of the compound (I-1).

Apoptosis is measured by using the kit "Apo-one homogeneous caspase-3/7 assay" (Promega Co., WI, USA) by following the recommendations of the manufacturer. Briefly, the cells are sown in 96-well culture plates with 50,000 cells per well in 100 µL of culture medium. After 24 hours of incubation, the medium is replaced with 100 µL of culture medium containing different concentrations of the compound (O-1) or 0.1% DMSO (negative control). After 24 hours of treatment, 100 µL of reagent containing the substrate of the caspase and the buffer of the reaction are added into each well. After 1 hour of incubation, the fluorescence emitted by the cell is measured at 527 nm with a microplate reader of the Victor type (Perkin-Elmer, USA).

Figure 2:
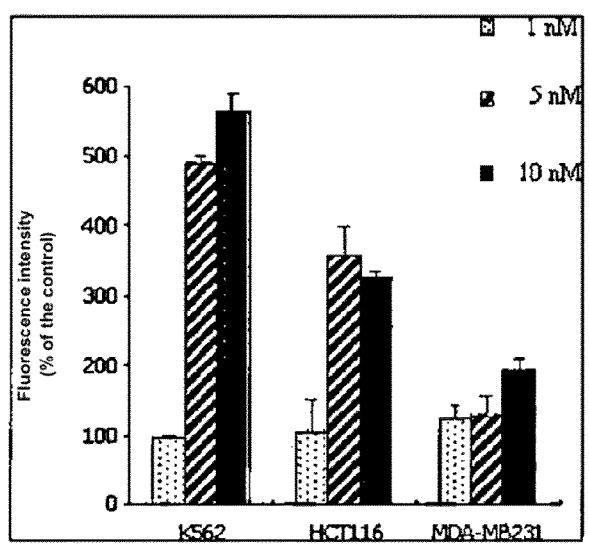

The results presented in FIG. 2 show that the incubation of the different cells with the compound (I-1) leads to strong induction of apoptosis.

EXAMPLE 3

Study of Inhibition of Polymerization of Tubulin

Tests relating to the inhibition of polymerization of tubulin were carried out on compounds which had the best cytotoxic activities. These tests were carried out on purified tubulin by the Shelanski method (Shelanski, M. C.; Gaskin, F.; Cantor, C. R. *Proc. Natl. Acad. Sci.* USA, 1973, 70, 765-768) from pig brains, where it forms 20-25% of the soluble proteins. Purification method is based on temperature-dependent assembling-disassembling cycles. Polymerization of tubulin was tracked with turbidimetry according to the Gaskin method (Gaskin, F.; Cantor, C. R.; Shelanski, M. L. *J. Bio. Mol.* 1974, 89, 737) at a wavelength of 350 nm. The different samples were dissolved in DMSO and incubated for 10 minutes at 37° C. and then for 5 minutes at 0° C.

The CA-4 compound and DMSO were taken as references.

The tests have shown for these compounds an activity inhibiting polymerization of tubulin similar to the one of the reference compound CA-4 (of the order of only one micromolar concentration to a few tens of micromolar concentrations). The obtained results are shown in the following Table 3.

TABLE 3

| Molecules of the invention | Inhibition of tubulin ($IC_{50}$ in µM) |
|---|---|
| (I-1) | 2.2 |
| (I-2) | 2.0-3.3 |
| (I-17) | 1.8 |
| (I-22) | 4.1 |

EXAMPLE 4

Figure 3:
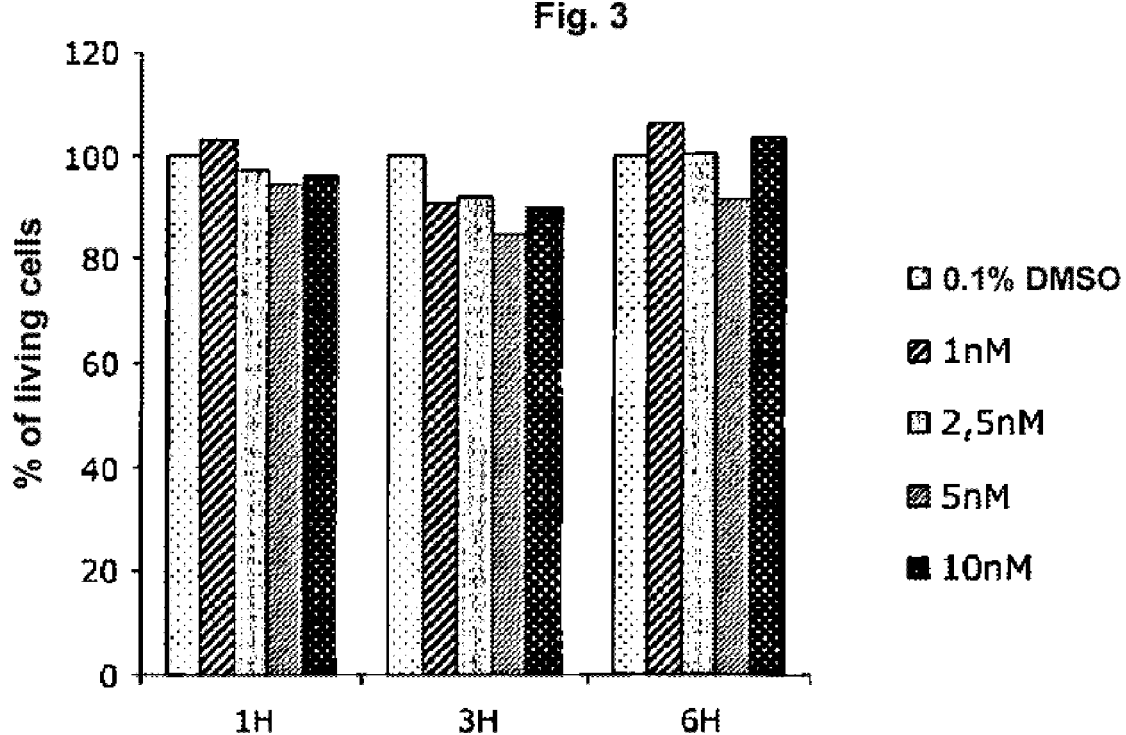
FIG. 3 illustrates the cytotoxic activity of the compound (I-1) on human endothelial cells EAhy926, measured immediately at the end of the treatment with the compound (I-1).
Figure 4:
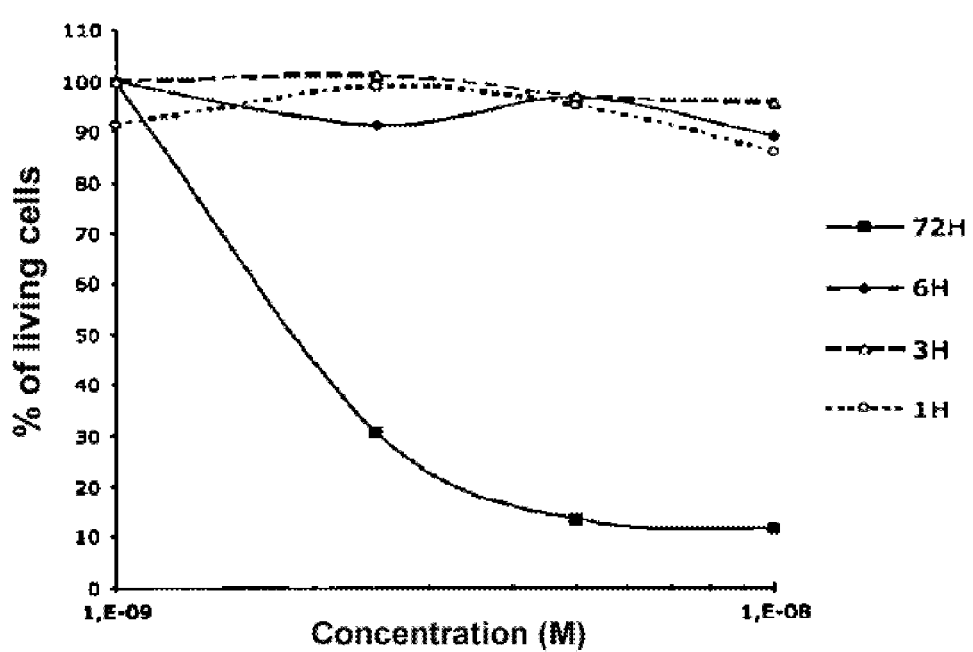
FIG. 4 illustrates the cytotoxic activity of the compound (I-1) on human endothelial cells EAhy926 measured after 72 hours ($IC_{50}$=2 nm).

Study of Anti-Vascular Activity 4.1. In Vitro Study of Cytotoxicity on Human Endothelial Cells Cytotoxicity of compound (I-1) towards human endothelial cells (EAhy926) was evaluated after 1 hour, 3 hours and 6 hours of treatment. The number of living cells was either counted immediately at the end of the treatment (FIG. 3) or 72 hours after stopping the treatment (FIG. 4). It is observed that when the endothelial cells are treated for 72 hours with the compound (I-1), the $IC_{50}$ is 2 nM. On the other hand, after 1 hour, 3 hours or 6 hours of treatment, the compound (I-1) does not exhibit any cytotoxic activity even at a dose of 10 nM.

4.2. In Vitro Study on the Formation of Vascular Tubes on Matrigel®

In order to know whether the compound (I-1) perturbs the spatial organization of endothelial cells in structures similar to vascular capillaries, human endothelial cells (EAhy926) were treated immediately after cultivation on Matrigel® or after 24 hours of cultivation, in order to allow them to form vascular tubes.

The EAhy926 cells (immortalized HUVEC macrovascular endothelial cells) were cultivated in a culture medium "Dulbecco minimal essential medium" (DMEM) containing 4.5 g/L of glucose and supplemented with 10% fetal calf serum, 1% glutamine and a supplement of HAT (100 µM of hypoxanthine, 0.4 µM of aminopterin and 16 µM of thymidine, Invitrogen; Cergy-Pontoise, France). The cells were maintained in the culture at 37° C. in a humid atmosphere containing 5% $CO_2$.

The cells were sown in 96-well culture plates in an amount of 3,000 cells per well in 50 µL of culture medium. After 24 hours of incubation, the compound (I-1) was added at different concentrations for 1 hour, 3 hours, 6 hours or 72 hours. At the end of the treatment, the number of cells was evaluated by using the reagent "CellTiter-Blue™" (Promega, Wis., USA) as described earlier. In parallel, after 1 hour, 3 hours or 6 hours of treatment with compound (I-1), the culture medium was removed and replaced with fresh medium for 72 hours and the number of living cells was then measured by using the reagent "CellTiter-Blue™".

In order to evaluate the antivascular activity of the compound (I-1), the EAhy926 cells were cultivated in 96-well culture plates covered beforehand with an extract of extracellular matrix (Matrigel™, BD Biosciences, Le Pont-de-Claix, France) in which they spontaneously form capillary tubes.

First of all, we measured the capacity of the compound (I-1) of inhibiting the formation of the capillary network. Matrigel™ is deposited in 96-well culture plates in an amount of 70 µL/well and left to incubate at 37° C. for 45 minutes in order to allow its polymerization. 15,000 cells suspended in 150 µL of culture medium are sown per well in each of the wells containing Matrigel™ in the absence or in the presence of different concentrations of the compound (I-1), with 3 wells per concentration. After 1 hour, 3 hours and 6 hours of incubation at 37° C., the cells are observed and photographed by means of an optical microscope of the TE2000 type (Nikon, France), equipped with a camera.

At the same time, 15,000 EAhy926 cells suspended in 150 µL of culture medium were sown in each of the wells containing Matrigel™. After 18 hours of incubation, when the capillary network is well formed, the compound (I-1) was added at different concentrations. The effect of the product was observed after 1 hour, 3 hours and 6 hours of incubation with an optical microscope.

It may be observed that after a treatment of 3 hours at a dose of 10 nM (non-toxic), the compound (I-1) induces a very significant decrease in the number of vascular tubes. These results indicate that the compound (I-1) also has antivascular activity potentially useful in therapy.

EXAMPLE 5

Study of the Antivascular Activity of the Molecule (I-1) In Vivo

The antivascular effect of the molecule (I-1) was tested on mice bearing human tumors by comparison with the positive control DMXAA, according to the procedure described by Beauregard et al. (*NMR Biomed.*, 2002, 15:99-105).

Figure 5:
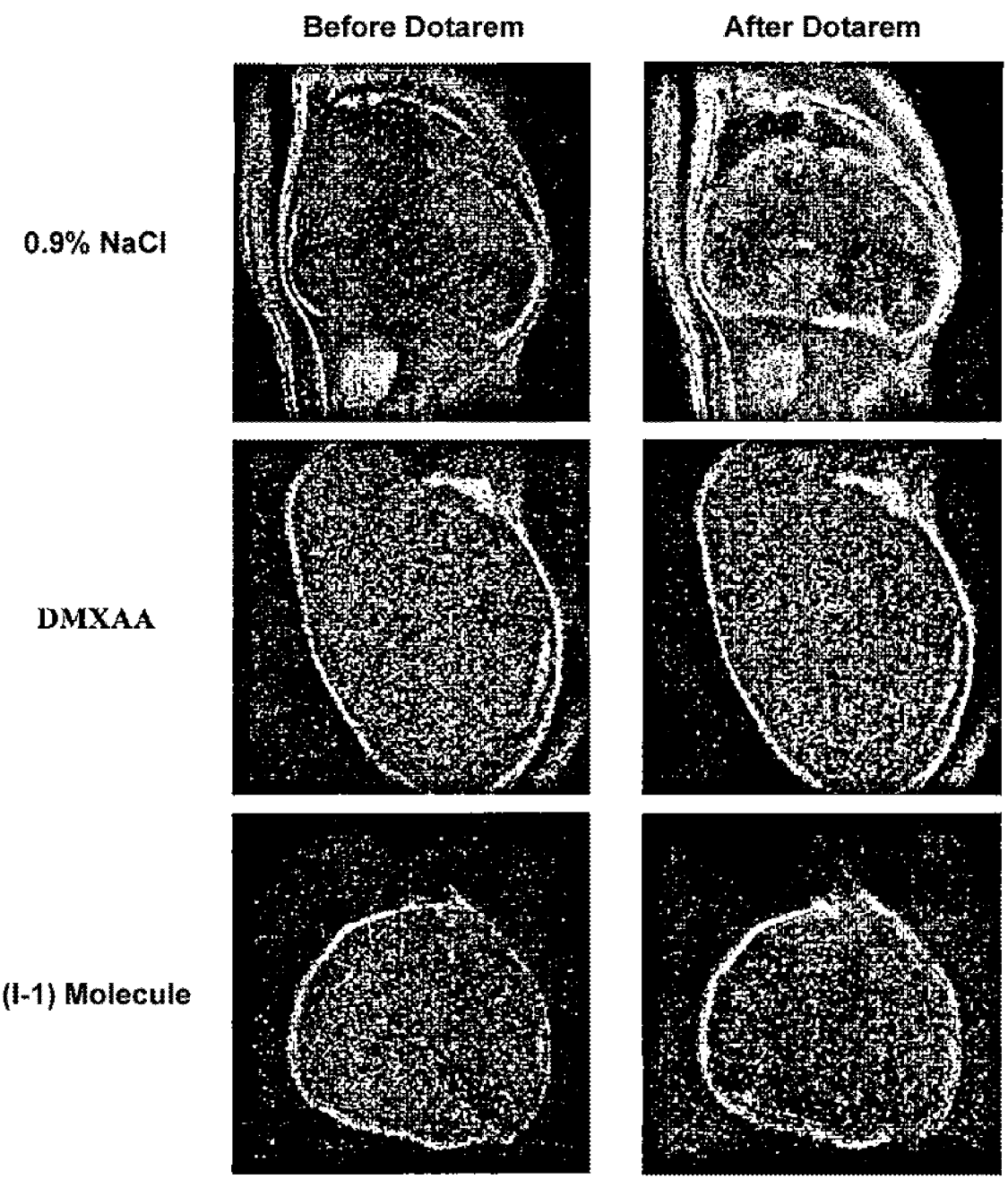
FIG. 5 illustrates the antivascular activity of the compound (I-1), as compared with 0.9% NaCl and with DMXAA, in Nude mice and illustrates photographs obtained by magnetic resonance imaging of tumors before and after injection of Dotarem.

Thus, CD-1 Nude female mice were xenografted by subcutaneous injection of human colon tumoral cells (LS174T). The mice bearing tumors were then treated with 0.9% NaCl (carrier, 10 mL/kg), DMXAA (27.5 mg/kg) via an intraperitoneal route (IP) or the molecule (I-1) (45 mg/kg) via an intravenous route (IV). Three hours after administration, the mice were treated with the Dotarem® contrast agent intravenously (IV). The penetration of the contrast agent into the tumors was followed in real time by magnetic resonance imaging (MRI) and is expressed by an enhancement of the intensity of the signal in the tumors. Densitometric analysis of the acquired images allows determination of the maximum enhancement (Rmax) as well as the slope P0 corresponding to the entry rate of Dotarem® into the tumors. These results are shown in the following Table 2. Characteristic images of the observed effects are also shown in FIG. 5.

TABLE 2

| Treatment (dose, administration route) | Average of Rmax (% of the NaCl control) | Average of P0 (arbitrary unit) | Number of mice analyzed per group |
|---|---|---|---|
| 0.9% NaCl (10 mL/kg, IP) | 100.00 ± 49.01 | 1.97 ± 0.96 | 5/8 |
| DMXAA (27.5 mg/kg, IP) | 26.58 ± 21.19 | 0.50 ± 0.40 | 4/8 |
| (I-1) (45 mg/kg, IV) | 67.56 ± 33.10 | 1.53 ± 0.82 | 6/8 |

The average Rmax was 100.00±49.01% in the group treated with 0.9% NaCl (n=5). The slope P0 was 1.97±0.96 (arbitrary unit).

These two parameters were strongly reduced in animals having received DMXAA (Rmax of 26.58±21.19% and P0 of 0.50±0.40; n=4); this expressing a reduction in the entry of Dotarem® in the tumors and therefore an effect of DMXAA on vascularization of the tumors.

The molecule (I-1) administered at 45 mg/kg produced a comparable effect by causing the lowering of the average Rmax to 67.56±33.10% and of the slope P0 to 1.53±0.82 (n=6). Thus, the molecule (I-1) has an antivascular effect on human colon tumors LS174T xenografted in Nude mice.

The invention claimed is:

1. A compound of the following formula (I):

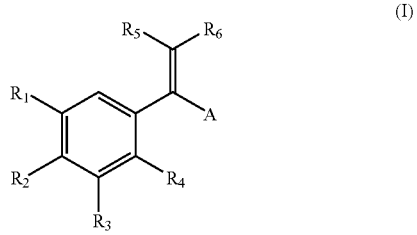

wherein:
$R_1$, $R_2$ and $R_3$ represent independently of each other a methoxy group optionally substituted with one or more fluorine atoms,
$R_4$ represents a hydrogen atom,
$R_5$ and $R_6$ are identical and each represents a hydrogen or fluorine atom,
A is a 1,3-benzodioxolyl, chromanyl or chromenyl group, said group being optionally substituted with one or more $C_1$-$C_4$ alkyl groups, or
a phenyl or naphtyl group, said group being optionally substituted with one or more groups selected from halogens, —B(OH)$_2$ groups, $C_1$-$C_4$ alkyls, $C_2$-$C_4$ alkenyls, $C_2$-$C_4$ alkynyls, aryl, heteroaryl, —COOH, —NO$_2$, methylenedioxy, —NR$_7$R$_8$, —NHCOR$_7$, —CONR$_7$R$_8$, —NHCOOR$_9$, —OSi($C_1$-$C_4$ alkyl)$_3$, —NHSO$_2$R$_9$, $C_1$-$C_4$ alkoxy optionally substituted with one or more fluorine atoms, OCONR$_7$R$_8$, —OSO$_2$CF$_3$, —OSO$_2$R$_9$, —SO$_2$R$_9$, —OSO$_3$H, —OPO(OR$_{10}$)$_2$, —ONR$_7$R$_8$, —OR$_{11}$, —SO$_2$NR$_{12}$R$_{13}$, —SO$_2$NHCOR$_{14}$, —OCOR$_{15}$, —OCOOR$_{16}$, —SR$_{17}$, OCO(CH$_2$)$_n$C$_6$H$_4$N[(CH$_2$)$_m$Cl]$_2$ with n=1 to 4 and m=1 to 3, and a residue of a molecule with antitumoral activity, said molecule comprising a COOH function in order to bound said molecule to the phenyl or naphtyl group via an ester or amide bond, wherein:
$R_7$ and $R_8$ represent independently of each other, a hydrogen atom or a $C_1$-$C_4$ alkyl, aryl or heteroaryl group,
$R_9$ represents a $C_1$-$C_4$ alkyl, aryl or heteroaryl group,
$R_{10}$ represents a hydrogen atom or a $C_1$-$C_4$ alkyl group or a benzyl group,
$R_{11}$ represents a hydrogen atom, an O-protective group, a sugar selected from glucose, mannose, arabinose or galactose, an aminosugar or an amino acid, the free OH and HN$_2$ groups of sugars, aminosugars and amino acids may optionally be substituted with an O-protective and N-protective group, respectively,
$R_{12}$ and $R_{13}$ represent independently of each other a hydrogen atom, a $C_1$-$C_4$ alkyl group, an aryl or heteroaryl group,
—COR$_{14}$ represents the remainder of an amino acid molecule bound to the —SO$_2$NH-group, or $R_{14}$ represents a $C_1$-$C_4$ alkyl group,
$R_{15}$ represents a hydrogen atom, a $C_1$-$C_4$ alkyl, aryl or heteroaryl group, or a (CH$_2$)$_m$CO$_2$H or —(CH$_2$)$_m$NR$_7$R$_8$ group with m=1 to 3,
$R_{16}$ represents a $C_1$-$C_4$ alkyl, aryl or heteroaryl group or a —(CH$_2$)$_m$CO$_2$H or —(CH$_2$)$_m$NR$_7$R$_8$ group with m=1 to 3, and
$R_{17}$ represents a hydrogen atom or a $C_1$-$C_4$ alkyl or aryl group, as well as its pharmaceutically acceptable salts, excluding the following compound:

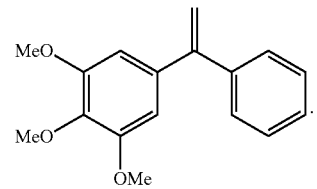

2. The compound according to claim 1, wherein the molecule with an antitumoral activity is selected from methotrexate, raltitrexed, melphalan, chlorambucil, L-asparaginase, (Z)-3-[2,4-dimethyl-5-(2-oxo-1,2-dihydro-indol-3-ylidenemethyl)-1H-pyrrol-3-yl]-propionic acid, 4-((9-chloro-7-(2,6-difluorophenyl)-5H-pyrimidol(5,4-d)(2)benzazepin-2-yl)amino)benzoic acid, 5,6-dimethylxanthenone-4-acetic acid and 3-(4-(1,2-diphenylbut-1-enyl)phenyl)acrylic acid.

3. The compound according to claim 1, wherein A is a ring selected from phenyl and naphtyl groups, and said ring may be substituted with one or more groups selected from -Me, —OH, —OMe, —OCF$_3$, —NH$_2$, —NO$_2$, —COOH, —B(OH)$_2$, —OSitBuMe$_2$, —OCOMe, —OCOtBu, methylenedioxy, —OCONEt2, —OCO(CH$_2$)$_2$COOH, —OCOCH$_2$NMe$_2$, —OSO$_3$H, —OSO$_2$CF$_3$, —OP(O)(OH)$_2$, —OP(O)(OEt)$_2$, OPO(OCH$_2$Ph)$_2$, —Br, —F, —OCO(CH$_2$)$_3$C$_6$H$_4$N[(CH$_2$)$_2$Cl]$_2$, —OCO(C$_5$H$_4$N),

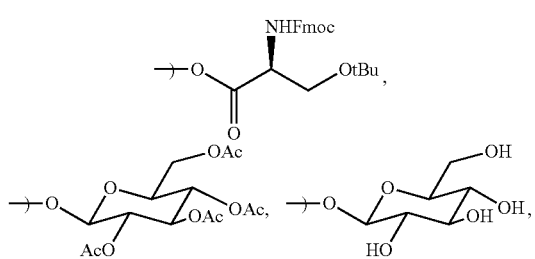

-continued

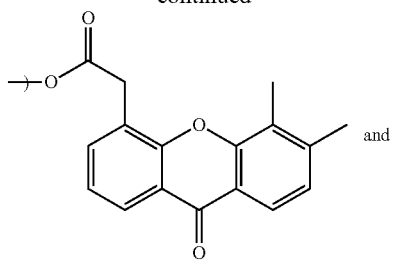

and

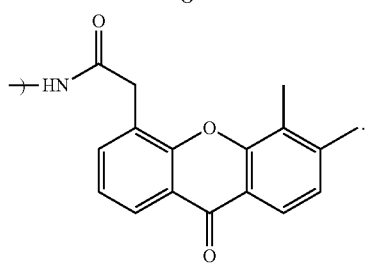

4. The compound according to claim 1, wherein it fits the following formula (II):

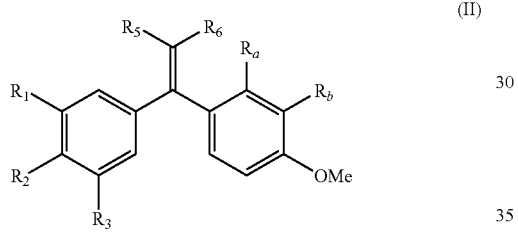

wherein:

$R_1$, $R_2$, $R_3$, $R_5$ and $R_6$ are as defined in claim 1,

Ra represents a hydrogen or halogen atom, or a group —B(OH)$_2$, C$_1$-C$_4$ alkyls, C$_2$-C$_4$ alkenyls, C$_2$-C$_4$ alkynyls, aryl, heteroaryl, —COOH, —NO$_2$, methylenedioxy, —NR$_7$R$_8$, —NHCOR$_7$, —CONR$_7$R$_8$, —NHCOOR$_9$, —OSi(C$_1$-C$_4$ alkyl)$_3$, —NHSO$_2$R$_9$, C$_1$-C$_4$ alkoxy optionally substituted with one or more fluorine atoms, —OCONR$_7$R$_8$, —OSO$_2$CF$_3$, —OSO$_2$R$_9$, SO$_2$R$_9$, —OSO$_3$H, —OPO(OR$_{10}$)$_2$, —ONR$_7$R$_9$, —OR$_{11}$, —SO$_2$NR$_{12}$R$_{13}$, —SO$_2$NHCOR$_{14}$, —OCOR$_{15}$, —OCOOR$_{16}$, —SR$_{17}$, or —OCO(CH$_2$)$_n$ C$_6$H$_4$N[(CH$_2$)$_m$Cl]$_2$ with n=1 to 4 and m=1 to 3, $R_a$ advantageously representing a hydrogen atom, and Rb represents a halogen atom, a —OR$_{11}$, —OCOR$_{15}$, —OCOOR$_{15}$, —OCONR$_7$R$_9$, —OSO$_2$R$_9$, —OSO$_2$CF$_3$, —OSO$_3$H, —OPO(OR$_{10}$)$_2$, —NH$_2$, —NHCOR$_7$, —NHCOOR$_9$, —NHSO$_2$R$_9$ group, or a residue of a molecule with antitumoral activity, said molecule comprising a COOH function in order to bound said molecule to the phenyl or naphtyl group via an ester or amide bond, $R_7$, $R_8$, $R_9$, $R_{10}$, $R_{11}$, $R_{12}$, $R_{13}$, $R_{14}$, $R_{15}$, $R_{16}$ and $R_{17}$ being as defined in claim 1.

5. The compound according to claim 1 wherein it is selected from:

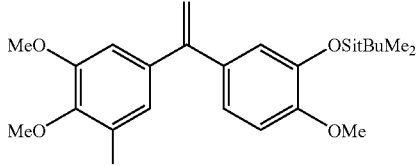

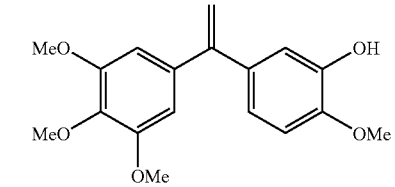

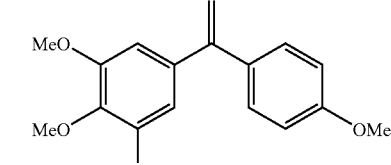

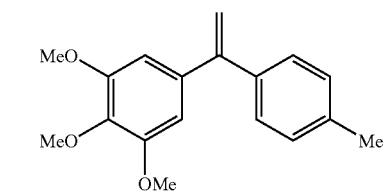

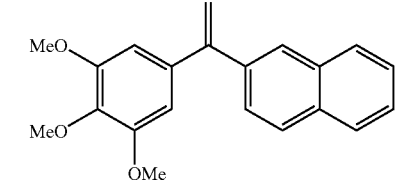

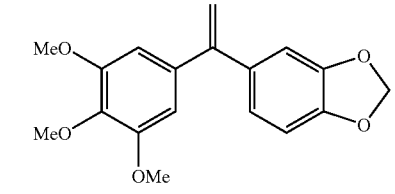

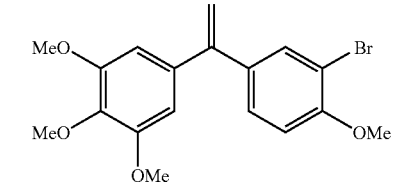

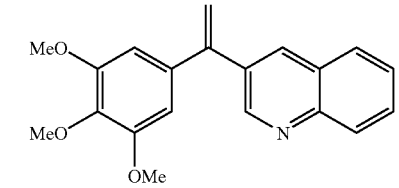

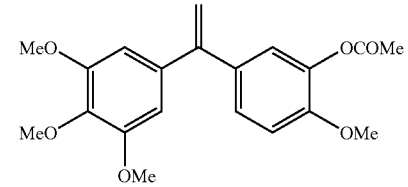

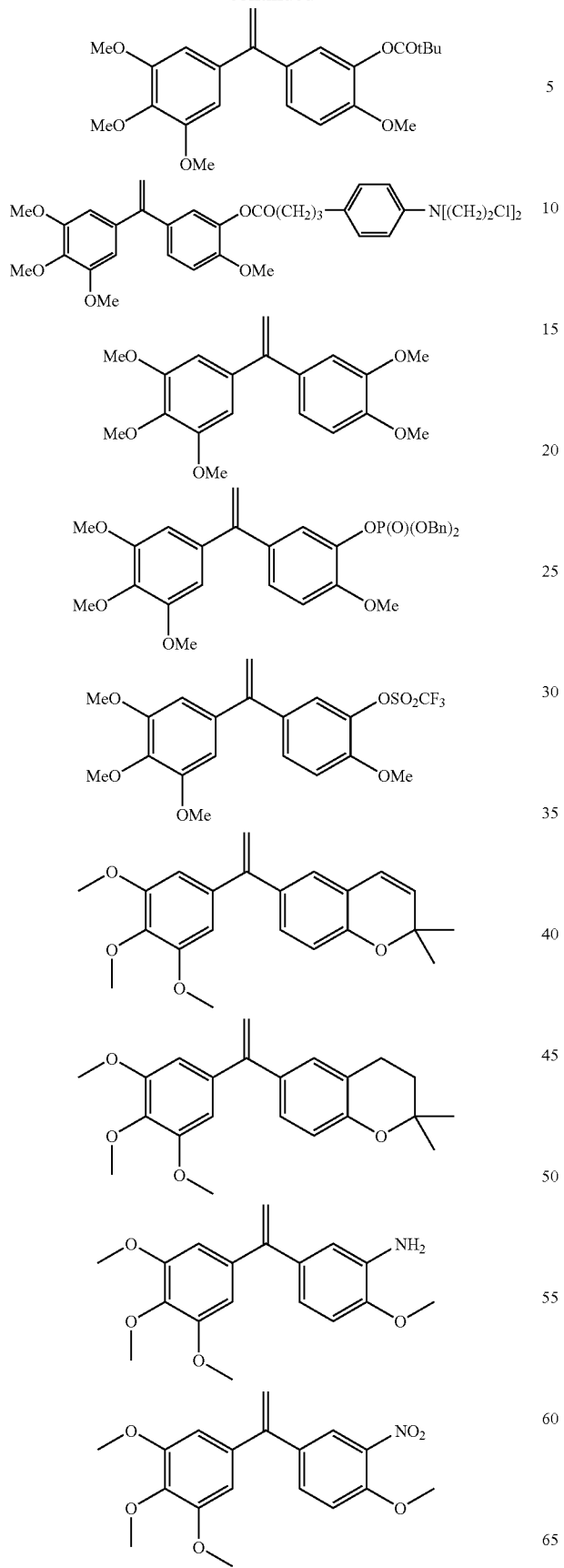
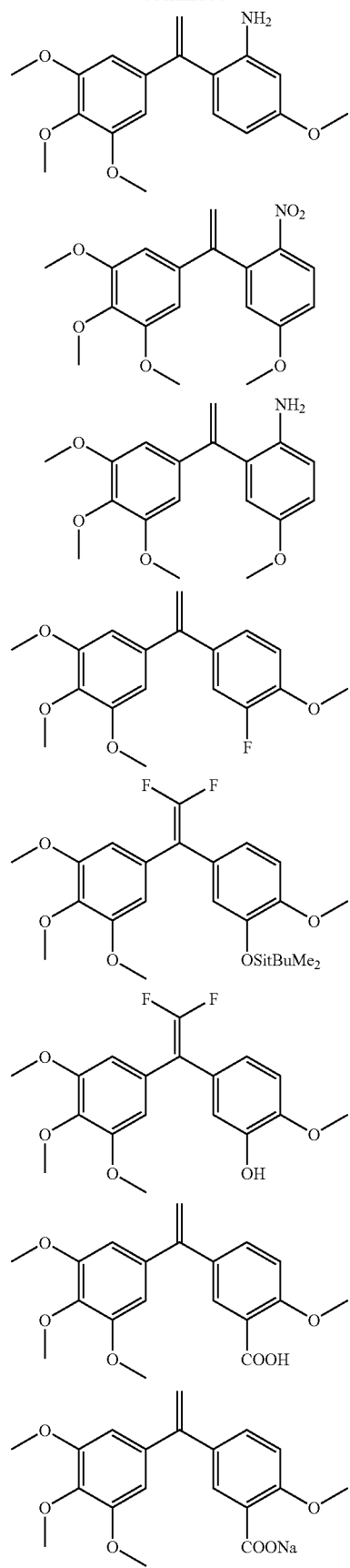

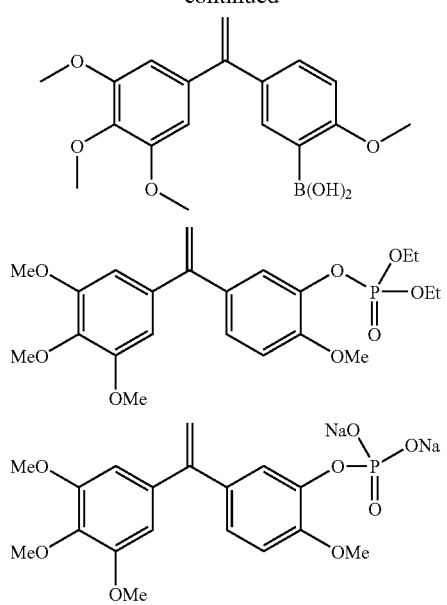
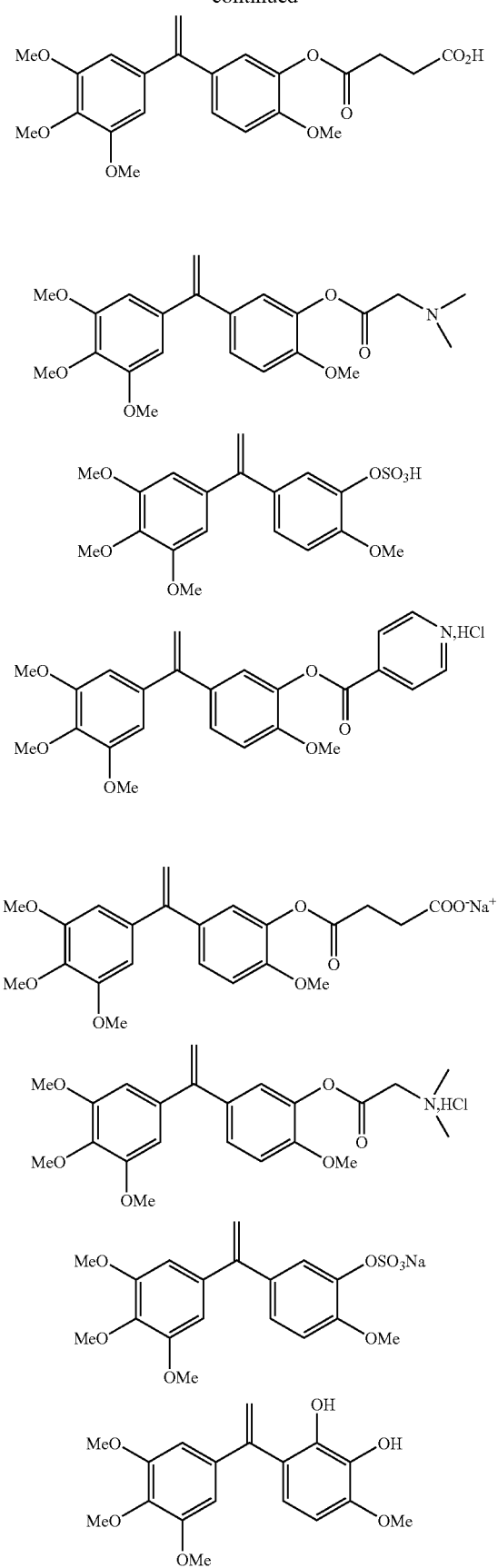

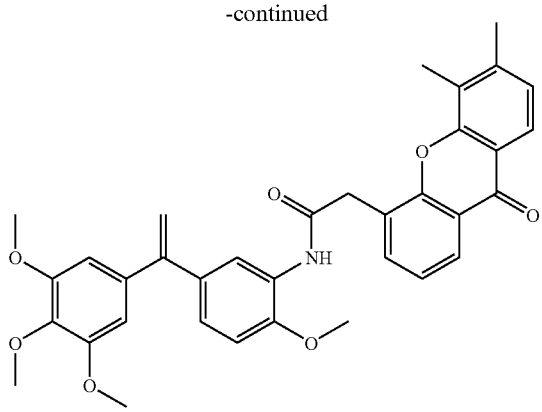

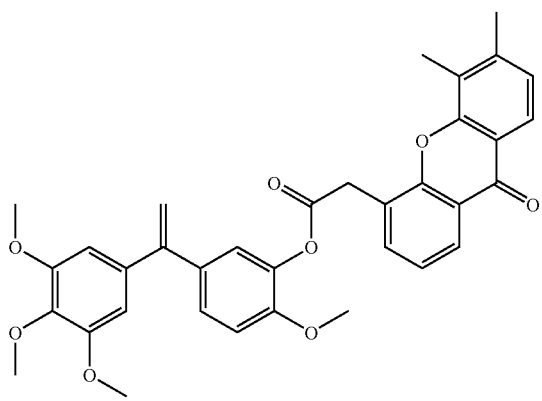

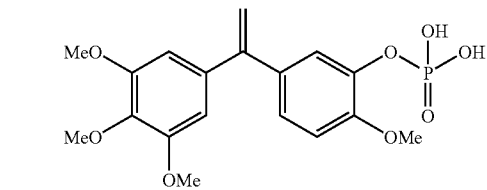

6. A method for preparing a compound of formula (I) as defined in claim 1, wherein said method comprises the following successive steps:
reacting a compound of the following formula (II):

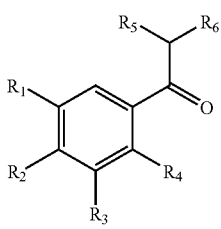

wherein $R_1$, $R_2$, $R_3$, $R_4$, $R_5$ and $R_6$ are as defined in claim 1, with an organometallic compound of formula A-M wherein A is as defined in claim 1 and M represents an alkaline metal or an earth alkaline metal substituted with a halogen, in order to form a compound of the following formula (III):

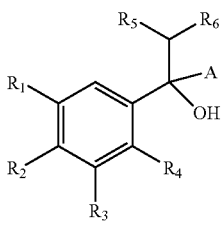

reacting the compound of formula (III) with an acid in order to form a compound of formula (I).

7. A method for inhibiting polymerization of tubulin comprising the administration to a person in need thereof of an effective amount of a compound according to claim 1 or a compound of the following formula:

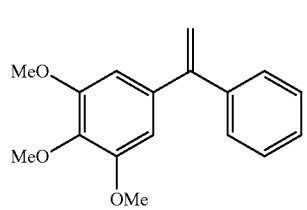

or a pharmaceutically acceptable salt thereof.

8. A method for treating or a proliferative disease comprising the administration to a person in need thereof of an effective amount of a compound according to claim 1 or a compound of the following formula:

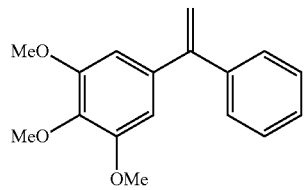

or a pharmaceutically acceptable salt thereof.

9. A pharmaceutical composition, comprising at least one compound according to claim 1 or a compound of the following formula:

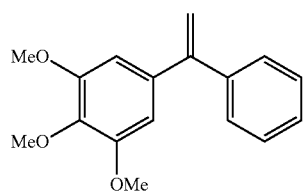

or a pharmaceutically acceptable salt thereof, in association with one or more pharmaceutically acceptable excipients.

10. The pharmaceutical composition according to claim 9, further compromising at least one other active ingredient.

11. The pharmaceutical composition according to claim 10, wherein the active ingredient is selected from 6-mercaptopurine, fludarabine, cladribine, pentostatin, cytarabine, 5-fluorouracil, gemcitabine, methotrexate, raltitrexed, irinotecan, topotecan, etoposide, daunorubicin, doxorubicin, epirubicin, idarubicin, pirarubicin, mitoxantrone, chlormethine, cyclophosphamide, ifosfamide, melphalan, chlorambucil, busulfan, carmustine, fotemustine, streptozocine, carboplatine, cisplatine, oxaliplatine, procarbazine, dacarbazine, bleomycin, vinblastine, vincristine, vindesine, vinorelbine, paclitaxel, docetaxel, L-asparaginase, flutamide, nilutamide, bicalutamide, cyproterone acetate, triptorelin, leuprorelin, goserelin, buserelin, formestane, aminoglutethimide, anastrazole, letrozole, tamoxifene, octreotide, lanreotide, (Z)-3-[2,4-dimethyl-5-(2-oxo-1,2-dihydro-indol-3-ylidenemethyl)-1H-pyrrol-3-yl]-propionic acid, 4-((9-chloro-7-(2,6-difluorophenyl)-5H-pyrimidol(5,4-d) (2)benzazepin-2-yl) amino)benzoic acid, 5,6-dimethylxanthenone-4-acetic acid and 3-(4-(1,2-diphenylbut-1-enyl)phenyl)acrylic acid.

12. A pharmaceutical composition comprising:
(i) at least one compound according to claim 1 or a compound of the following formula:

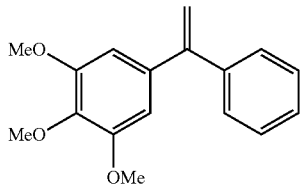

or a pharmaceutically acceptable salt thereof,
(ii) at least one other active ingredient,
as combination products for simultaneous, separate use, or use spread out over time.

13. The composition according to claim 12, wherein the active ingredient(s) is(are) selected from 6-mercaptopurine, fludaribine, cladribine, pentostatin, cytarabine, 5-fluorouracil, gemcitabine, methotrexate, raltitrexed, irinotecan, topotecan, etoposide, daunorubicin, doxorubicin, epirubicin, idarubicin, pirarubicin, mitoxantrone, chlormethine, cyclophosphamide, ifosfamide, melphalan, chlorambucil, busulfan, carmustine, fotemustine, streptozocine, carboplatine, cisplatine, oxaliplatine, procarbazine, dacarbazine, bleomycin, vinblastine, vincristine, vindesine, vinorelbine, paclitaxel, docetaxel, L-asparaginase, flutamide, nilutamide, bicalutamide, cyproterone acetate, triptorelin, leuprorelin, goserelin, buserelin, formestane, aminoglutethimide, anastrazole, letrozole, tamoxifene, octreotide, lanreotide, (Z)-3-[2,4-dimethyl-5-(2-oxo-1,2-dihydro-indol-3-ylidenemethyl)-1H-pyrrol-3-yl]-propionic acid, 4-((9-chloro-7-(2,6-difluorophenyl)-5H-pyrimidol(5,4-d) (2)benzazepin-2-yl) amino)benzoic acid, 5,6-dimethylxanthenone-4-acetic acid and 3-(4-(1,2-diphenylbut-1-enyl)phenyl)acrylic acid.

14. The compound according to claim 1, wherein $R_1$, $R_2$ and $R_3$ each represents a methoxy group.

15. The compound according to claim 1, wherein $R_5$ and $R_6$ each represents a hydrogen atom.

16. The compound according to claim 1, wherein $R_7$ and $R_8$ represent a hydrogen atom or a $C_1$-$C_4$ alkyl group.

17. The compound according to claim 1, wherein $R_9$ represents a $C_1$-$C_4$ alkyl group.

18. The compound according to claim 1, wherein A is:
a 1,3-benzodioxolyl, chromanyl or chromenyl group, said group being optionally substituted with one or more $C_1$-$C_4$ alkyl groups, a phenyl group optionally substituted with one or more groups selected from halogens, —B(OH)$_2$ groups, $C_1$-$C_4$ alkyls, $C_2$-$C_4$ alkenyls, $C_2$-$C_4$ alkynyls, aryl, heteroaryl, —COOH, —NO$_2$, methylenedioxy, —NR$_7$R$_8$, —NHCOR$_7$, —CONR$_7$R$_8$, —NHCOOR$_9$, —OSi(C$_1$-C$_4$ alkyl)$_3$, —NHSO$_2$R$_9$, $C_1$-$C_4$ alkoxy optionally substituted with one or more fluorine atoms, —OCONR$_7$R$_8$, —OSO$_2$CF$_3$, —OSO$_2$R$_9$, —SO$_2$R$_9$, —OSO$_3$H, —OPO(OR$_{10}$)$_2$, —ONR$_2$R$_8$, —OR$_{11}$, —SO$_2$NR$_{12}$R$_{13}$, SO$_2$NHCOR$_{14}$, —OCOR$_{15}$, —OCOOR$_{16}$, —SR$_{17}$, —OCO(CH$_2$)$_n$C$_6$H$_4$N[(CH$_2$)$_m$Cl]$_2$ with n=1 to 4 and m=1 to 3, and a residue of a molecule with antitumoral activity, said molecule comprising a COOH function in order to bound said molecule to the phenyl or naphtyl group via an ester or amide bond, $R_7$, $R_8$, $R_9$, $R_{10}$, $R_{11}$, $R_{12}$, $R_{13}$, $R_{14}$, $R_{15}$, $R_{16}$, and $R_{17}$ being as defined in claim 1.

19. The compound according to claim 3, wherein A is a phenyl ring, wherein said ring may be substituted with one or more groups selected from -Me, —OH, —OMe, —OCF$_3$, —NH$_2$, —NO$_2$, —COOH, —B(OH)$_2$, OSitBuMe$_2$, —OCOMe, —OCOtBu, methylenedioxy, —OCONEt$_2$, —OCO(CH$_2$)$_2$COOH, —OCOCH$_2$NMe$_2$, —OSO$_3$H, —OSO$_2$CF$_3$, —OP(O)(OH)$_2$, —OP(O)(OEt)$_2$, —OPO(OCH$_2$Ph)$_2$, —Br, —F, —OCO(CH$_2$)$_3$C$_6$H$_4$N[(CH$_2$)$_2$Cl]$_2$, —OCO(C$_5$H$_4$N),

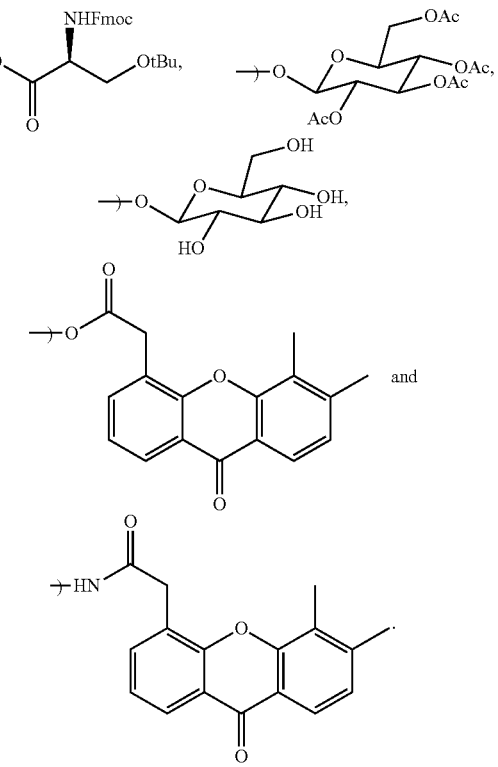

20. The method according to claim 8, wherein the proliferative disease is cancer, psoriasis or fibrosis.

* * * * *